United States Patent [19]
Wang et al.

[11] Patent Number: 5,968,802
[45] Date of Patent: Oct. 19, 1999

[54] NUCLEAR CYCLOPHILIN

[76] Inventors: Bruce Wang, 1123 Banyan Way, Pacifica, Calif. 94044; Donald Payan, 24 Windsor Dr., Hillsborough, Calif. 94010; Joseph Fisher, 1035 S. Van Ness Ave., Apt. D, San Francisco, Calif. 94110

[21] Appl. No.: 08/482,728

[22] Filed: Jun. 7, 1995

[51] Int. Cl.$^6$ ............................... C12N 9/90; C12N 1/21; C12N 15/63; C07H 21/04

[52] U.S. Cl. ................. 435/233; 435/252.3; 435/254.11; 435/320.1; 536/23.2

[58] Field of Search ................................. 435/233, 320.1, 435/252.3, 254.11; 536/23.2

[56] References Cited

FOREIGN PATENT DOCUMENTS

WO 94/10300  5/1994  WIPO .

OTHER PUBLICATIONS

Thall, M., et al., "Functional association of cyclophilin A with HIV–1 virions", *Nature,* 372:363–365 (1994).

Gabay, J. E., et al., "Antibiotic peptides and serine protease homologs in human polymorphonuclear leukocytes: defensins and azurocidin", *Current Opinion in Immunology,* 5:97–102 (1993).

Luban, J., et al., "Human Immunodeficiency Virus Type 1 Gag Protein Binds to Cyclophilins A and B", *Cell,* 73:1067–1078 (1993).

Stamnes, M. A., et al., "The Cyclophilin Homolog ninaA Is a Tissue–Specific Integral Membrane Protein Required for the Proper Synthesis of a Subset of Drosophila Rhodopsins", *Cell,* 65:219–227 (1991).

Franke, E. K., et al., "HIV–1 Uses Host–Cell Proteins To Form Fully Infectious Virions", *The Journal of NIH Research,* 7:37–42 (1995).

Liu, J., et al., "Human and *Escherichia coli* Cyclophilins: Sensitivity to Inhibition by the Immunosuppressant Cyclosporin A Correlates with a Specific Tryptophan Residue", *Biochemistry* 30:2306–2310 (1991).

Bram, R. J., et al., "Identification of the Immunophilins Capable of Mediating Inhibition of Signal Transduction by Cyclosporin A and FK506: Roles of Calcineurin Binding and Cellular Location", *Molecular and Cellular Biology,* 13(8):4760–4769 (1993).

Fields, S., et al., "A novel genetic system to detect protein–protein interactions", *Nature,* 340:245–246 (1989).

Azhderian, E. M., et al., "Nuclear Membrane–Associated Cyclophilins of Potential Importance in Cyclosporine Immunosuppression", *Transplantation Proceedings,* 25(1):524–526 (1993).

O'Keefe, S. J., et al., "FK–506–and CsA–sensitive activation of the interleukin–2 promoter by calcineurin", *Nature,* 357:692–694 (1992).

Clipsonte, N. A., et al., "Identification of calcineurin as a key signalling enzyme in T–lymphocyte activation", *Nature,* 357:695–697 (1992).

Vojtek, A. B., et al., "Mammalian Ras Interacts Directly with the Serine/Threonine Kinase Raf", *Cell,* 74:205–214 (1993).

Bram, R. J., et al., "Calcium signalling in T cells stimulated by a cyclophilin B–binding protein", *Nature,* 371:355–358 (1994).

Wang, T., et al., "Specific Interaction of Type I Receptors of the TGF–β Family with the Immunophilin FKBP–12", *Science,* 265:674–676 (1994).

(List continued on next page.)

*Primary Examiner*—Robert A. Wax
*Assistant Examiner*—Kawai Lau
*Attorney, Agent, or Firm*—Flehr Hobach Test Albritton & Herbert; David J. Brezner, Esq.; Robin M. Silva, Esq.

[57] ABSTRACT

Cyclophilin-60 proteins, nucleic acids, and monoclonal antibodies are provided.

13 Claims, 14 Drawing Sheets

(2 of 14 Drawing Sheet(s) Filed in Color)

```
289  GDLNLELHCDLTPKTCENFIRLC---KKHY--------YDGTIFHRSIRNFVIQGGDPTGT-GTGGES  hCyP-60

289  •P•••••FAPKV••A•••••TH•---SNG•---------•NN•K•••L•K••ML•••••••••H••••  CEF59E10_1
 10  ••IKI••YV•DA••A•••••LA••----ASD•---------•N•C••••N•KD•MV•T••••HS••K••••  CELB0252_4
500  ••IHTK•FPVEC•••V•••CVHS---RNG•---------•N•HT••I•KG•M••T•••••••-M••••  HUMORF006_1
 18  •RVSF••FA•KV•••A•••RA•STGE•GFG---------•K•SC•••I•PG•MC••••F•RHN••••K•  hCyPA
 50  •RVIFG•FGKTV••VD••VA•ATGE•GFG---------•KNSK•••V•KD•M•••••F•RGD••••K•  hCyPB
 52  •RIVIG•FGKVV•••V•••VA•ATGE•GYG---------•K•SK•••V•KD•M•••••I•TGD••••V•  hCyPC
 60  •RVVL••KA•VV•••A•••RA••TGE•GFG---------•K•ST•••V•PS•MC•A••F•NHN••••K•  hCyPD
 30  •RIV•••FA•IV•••A•••RA••TGE•GIGHTTGKPLHFK•CP•••I•KK•M•••••FSNQN••••••  hCyP-40
 75  •RIMFQ•FS•IC••••K••LC••SGE•GLGKTTGKKLC•K••VVK••M••••FSEGN•K••••  hNK-TR
 19  •RIVM••RS•VV•••A•••RA••TGE•GFG---------•K•SI•••V•P••MC••••F•NHN••••K•  Dros. CyP-1
 16  •RVVFK•YN•IV•••A•••RA••TGE•GFG---------•A•SP•••V•PD•ML•••••F•AGN••••K•  S. cer CyP-1

↓

YWGKPFKDEFRPNLSHTGRGILSMANSGPNSNRSQFFITFRSCAYLDKKHTIFGRVVGGFDVLTAME  hCyP-60

I•D•••S•••ISCF••DA••V•••••K•S•T•G•••••••P•K•••R••••••••L•••Q•T••TI•  CEF59E10_1
I••G••E•••VSA•K•DS••CV••••N••D•••••••••YAKQ•H••M•Y•L••K•ID•••T•EEI•  CELB0252_4
I••GE•E•••HST•R•DRPYT•••••A•S•T•G•••••••VVPTPW••N•••V••••TK•ME•VQRIS  HUMORF006_1
IY•EK•E•••NFI•K•••P••••••••A•••T•G••••••CTAKTEW••G••VV••K•KE•MNIVE•••  hCyPA
IY•ER•P•••NFK•K•Y•P•WV•••A•KDT•G••••••TVKTAW••G••VV••K•LE•ME•VRKV•  hCyPB
IY•ET•P•••NFK•K•Y•I•WV••••A••DT•G••••••LTKPTW••G••VV••K•ID•MT•VHSI•  hCyPC
IY•SR•P•••NFT•K•V•P•V••••••A•••T•G••••••CTIKTDW••G••VV••H•KE•M••VKKI•  hCyPD
IY•EK•E•••NFHYK•DRE•L•••••A•R•T•G••••••TVPTPH••G••VV••Q•IK•IG•ARIL•  hCyP-40
IY•GY•••••NFI•K•DRAFL•••••R•KHT•G••••••TKPAPH••GV•VV••L•IS••E•IEQI•  hNK-TR
IY•NK•P•••NFE•K•••S••••••••A•A•T•G••••••CTVKT•W••N••VV••E••E•L••VKKI•  Dros. CyP-1
IY•GK•P•••NFKKH•DRP•L••••••A•••T•G••••••TVP•PW••G••VV••E••D•Y•IVKKV•  S. cer CyP-1
```

OTHER PUBLICATIONS

Walsh, C. T., et al., "Cyclosporin A, the Cyclophilin Class of Peptidylprolyl Isomerases, and Blockage of T Cell Signal Transduction", *The Journal of Biological Chemistry*, 267(19):13115–13118 (1992).

Franke, E. K., et al., "Specific incorporation of cyclophilin A into HIV–1 virions", *Nature*, 372:359–362 (1994).

Sigal, N. H., et al., "Cyclosporin A, FK–506, and Rapamycin: Pharmacologic Probes of Lymphocyte Signal Transduction", *Annu. Rev. Immunol.*, 10:519–60 (1992).

Fruman, D. A., et al., "Immunophilins in protein folding and immunosuppression", *The FASEB Journal*, 8:391–400 (1994).

Snyder, S. H., et al., "Immunophilins and the nervous system", *Nature Medicine*, 1(1):32–37 (1995).

Liu, J., et al., "Calcineurin Is a Common Target of Cyclophilin–Cyclosporin A and FKBP–FK506 Complexes", *Cell*, 66:807–815 (1991).

Cullen, B. R., et al., "Chaperoning a pathogen", *Nature*, 372:319–320 (1994).

Trandinh, C. C., et al., "Structural and evolutionary relationships among the immunophilins: two ubiquitous families of peptidyl–prolyl cis–trans isomerases", *The FASEB Journal*, 6:3410–3420 (1992).

Rinfret, Aline, et al., "The N–Terminal Cyclophilin–Homologous Domain of a 150–Kilodalton Tumor Recognition Molecule Exhibits Both Peptidylprolyl cis–trans–Isomerase and Chaperone Activities." *Biochemistry*, 33(7):1668–1673 (1994).

Price, E. Roydon, et al., "Cyclophilin B Trafficking Through the Secretory Pathway is Altered by Binding of Cyclosporin A." *Proc. Natl. Acad. Sci. USA*, 91:3931–3935 (1994).

Nair, Asha P., et al., "Cyclosporin A Inhibits Growth of Autocrine Tumor Cell Lines by Destabilizing Interleukin–3 mRNA." *Nature*, 369:239–242 (1994).

Ryffel, B., et al., "Distribution of the Cyclosporin Binding Protein Cyclophilin in Human Tissues." *Immunology*, 72:399–404 (1991).

Schneider, Helmut, et al., "Human Cyclophilin C: Primary Structure, Tissue Distribution, and Determination of Binding Specificity for Cyclosporins." *Biochemistry*, 33:8218–8224 (1994).

Pflugl, Gaston, et al., "X–Ray Structure of a Decameric Cyclophilin–Cyclosporin Crystal Complex." *Nature*, 361:91–94 (1993).

Kahan, Barry D., "Cyclosporine." *Medical Intelligence*, 321(25):1725–1738 (1989).

Mason, June, "Pharmacology of Cyclosporine (Sandimmune) VII. Pahtophysiology and Toxicology of Cyclosporine in Humans and Animals." *Pharmacological Reviews*, 42(3):423–434 (1989).

Wilson, R., et al., "2.2 Mb of Contiguous Nucleotide Sequence from Chromosome III of *C. elegans*." *Nature*, 368:32–38 (1994).

Baker, E., "The Cyclophilin Homolog NinA Functions as a Chaperone, Forming a Stable Complex in vivo with its Protein Target Rhodopsin." *The EMBO Journal*, Sequencing Project submitted to the EMBL/GenBank/DDBJ databases.

Seemuller, Ursula, "Structure of the Elastase–Cathepsin G Inhibitor of the Leech *Hirudo medicinalis*." *Hoppe–Seyler's Z. Physiol. Chem.*, 361:1841–1846 (1980).

Price, E. Roydon, et al., "Human Cyclophilin B: A Second Cyclophilin Gene Encodes a Peptidyl–Prolyl Isomerase with a Signal Sequence." *Proc. Natl. Acad. Sci. USA*, 88:1903–1907 (1991).

Fischer, Gunter, "Cyclophilin and Peptidyl–Prolyl cis–trans Isomerase are Probably Identical Proteins." *Nature*, 337:476–478 (1989).

Freskgard, Per–Ola, "Isomerase and Chaperone Activity of Prolyl Isomerase in the Folding of Carbonic Anhydrase." *Science*, 258:466–468 (1992).

Emmel, Elizabeth A., "Cyclosporin A Specifically Inhibits Function of Nuclear Proteins Involved in T Cell Activation." *Science*, 246:1617–1620 (1989).

Nomura, N., et al., "Prediction of the Coding Sequences of Unidentified Human Genes. II. The Coding Sequences of 40 New Genes (KIAA 0041 –KIAA 0080) Deduced by Analysis of Randomly Sampled cDNA Clones from Human Immagure Myeloid Cell Line KGI." Unpublished (1994).

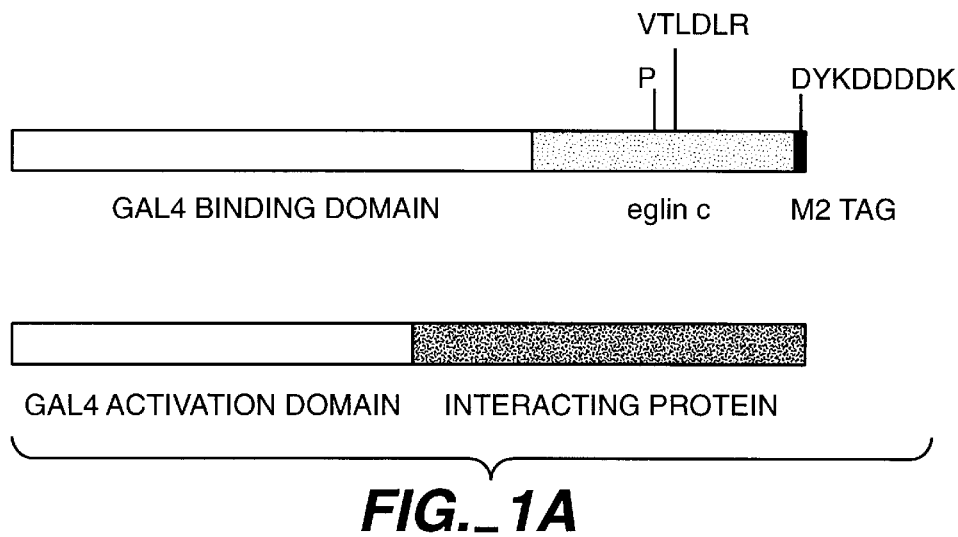
FIG._1A
| PLASMID 1 | PLASMID 2 | β-gal ASSAY (COLONY COLOR) |
|---|---|---|
| pBDeglin | (NONE) | white |
| (NONE) | pAD16.1 | white |
| pGBT9 | pAD16.1 | white |
| pVA3 | pAD16.1 | white |
| pVA3 | pTD1 | blue |
| pBDeglin | pAD16.1 | blue |
FIG._1B
|  | %Identity | Accession Number |
|---|---|---|
| hCyP-60 |  |  |
| CEF59E10_1 | 66 | Z36949/Z46935 |
| CELB0252_4 | 58 | U23453 |
| HUMORF006_1 | 51 | D38552 |
| hCyPA | 52 | Y00052 |
| hCyPB | 46 | M60457 |
| hCyPC | 48 | S71018 |
| hCyPD | 50 | M80254 |
| hCyP-40 | 50 | L11667 |
| hNK-TR | 48 | L04288 |
| Dros. CyP-1 | 54 | M62398 |
| S. cer CyP-1 | 50 | M30513 |
FIG._3B

```
CCCCCCCCC CCCCGAACTC GGCTGCGGCT CCATGGTCTG AGTTGTCAGC CGTTGTTTTT                    60

TCGTGCTCGC TAGTCGCCGC CGCCGCTCCG CC ATG GGG AAG CGA CAG CAC CAA                   113
                                    Met Gly Lys Arg Gln His Gln
                                     1               5

AAG GAC AAA ATG TAC ATT ACC TGT GCT GAA TAC ACT CAC TTT TAT GGT                   161
Lys Asp Lys Met Tyr Ile Thr Cys Ala Glu Tyr Thr His Phe Tyr Gly
             10                  15                  20

GGC AAG CCA GAT CTC CCA CAA ACA CAA TTT CGT CGT TTA CCT TTT                       209
Gly Lys Pro Asp Leu Pro Gln Thr Gln Phe Arg Arg Leu Pro Phe
         25                  30                  35

GAC CAC TGC AGT CTC TCT CTG CAG CCC TTT GTC TAC CCA GTC TGC ACT                   257
Asp His Cys Ser Leu Ser Leu Gln Pro Phe Val Tyr Pro Val Cys Thr
 40                  45                  50                  55

CCC GAT GGC ATC GTC TTT GAC TTA CTG AAC ATT GTT CCA CTT AAG                       305
Pro Asp Gly Ile Val Phe Asp Leu Leu Asn Ile Val Pro Trp Leu Lys
         60                  65                  70

AAG TAC GGG ACC AAC CCC AAT AGC GAG AAG AGT GAG AAG CTG GAC AGG GGG AGG TCC       353
Lys Tyr Gly Thr Asn Pro Asn Ser Lys Lys Ser Glu Lys Leu Asp Gly Arg Ser
             75                  80                  85

CTG ATC AAG CTG AAC TTT TCC AAG AAC ACC AAC ACC CAC TAC CAC TGC                   401
Leu Ile Lys Leu Asn Phe Ser Lys Asn Thr Asn Thr His Tyr His Cys
         90                  95                 100

CCA GTG CTG TTT ACC GTG TTC ACC AAC TTC ACC GTG ATC GTG GCT GTG                   449
Pro Val Leu Phe Thr Val Phe Thr Asn Phe Thr Val Ile Val Ala Val
105                 110                 115

AGG ACG ACC GGC AAC GTC TAC GCC TAT GAG GCA GTG GAA CAG CTA AAT                   497
Arg Thr Thr Gly Asn Val Tyr Ala Tyr Glu Ala Val Glu Gln Leu Asn
120                 125                 130                 135
```

FIG._2A

```
ATC AAG GCC AAG AAC TTC CGG GAC CTG ACC GAC GAG CCC TTC TCC                                  545
Ile Lys Ala Lys Asn Phe Arg Asp Leu Thr Asp Glu Pro Phe Ser
                140                 145                 150

CGG CAG GAC ATC ATC ACC CTC CAG GAC AAG CCC ACC AAT TTG GAC AAG TTC                          593
Arg Gln Asp Ile Ile Thr Leu Gln Asp Lys Pro Thr Asn Leu Asp Lys Phe
            155                 160                 165

AAT GTC TCT AAC TTC TAT CAT GTG AAG AAT AAC ATG AAA ATA ATA GAC                              641
Asn Val Ser Asn Phe Tyr His Val Lys Asn Asn Met Lys Ile Ile Asp
        170                 175                 180

CCA GAT GAA GAG AAG GCC AAG CAG GAC CCG TCT TAT TAT CTC AAA AAT                              689
Pro Asp Glu Glu Lys Ala Lys Gln Asp Pro Ser Tyr Tyr Leu Lys Asn
    185                 190                 195

ACA AAT GCC GAG ACC CGA GAG ATT CTG CAG ACC ATG AAG GCC CCG GAG AAG                          737
Thr Asn Ala Glu Thr Arg Glu Ile Leu Gln Thr Met Lys Ala Pro Glu
200                 205                 210                 215

AAA GGG GAC GAG ATT CTG GCA GCC ACC ATG GTC TAT TCC ACA GGG AAG GAG TTC                      785
Lys Gly Asp Glu Ile Leu Ala Ala Thr Met Val Tyr Ser Thr Gly Lys Glu Phe
                220                 225                 230

AAA GTG GAC AAG CTG AAT GCT CAC GCC ATG GTC CCG ATG GTC CCG AAG GTC AGC                      833
Lys Val Asp Lys Leu Asn Ala His Ala Met Val Pro Met Val Pro Lys Val Ser
        235                 240                 245

GCT TCC TTC ACC TCC ACC GCG ATG GTC CCG GAG ACC ACA CAT GAA GCA                              881
Ala Ser Phe Thr Ser Thr Ala Met Val Pro Glu Thr Thr His Glu Ala
250                 255                 260

GCT GCC ATC GAC GAG GAT GTG CTG CGC TAC CAG TTT GTG AAG AAG AAG                              929
Ala Ala Ile Asp Glu Asp Val Leu Arg Tyr Gln Phe Val Lys Lys Lys
    265                 270                 275
```

FIG._2B

```
GGC TAC GTG CGG CTG CAC ACC AAC AAG GGC GAC CTC AAC CTG GAG CTG    977
Gly Tyr Val Arg Leu His Thr Asn Lys Gly Asp Leu Asn Leu Glu Leu
280                     285                 290                 295

CAC TGC GAC CTG ACA CCA AAA ACC TGC GAA AAC TTC ATC AGG CTT TGC   1025
His Cys Asp Leu Thr Pro Lys Thr Cys Glu Asn Phe Ile Arg Leu Cys
        300                 305                 310

AAG CAT TAT TAC GAT GGC ACC ATC TTC CAC AGA TCC ATC CGG AAC       1073
Lys His Tyr Tyr Asp Gly Thr Ile Phe His Arg Ser Ile Arg Asn
315                 320                 325

TTT GTG ATC CAA GGG GGC GAC CCC ACA GGC ACG GGT GGG GAG           1121
Phe Val Ile Gln Gly Gly Asp Pro Thr Gly Thr Gly Gly Glu
        330                 335                 340

TCA TAC TGG GGG AAG CCC TTC AAA GAC GAG TTC CGG CCC AAC CTC TCG   1169
Ser Tyr Trp Gly Lys Pro Phe Lys Asp Glu Phe Arg Pro Asn Leu Ser
345                 350                 355

CAC ACG GGC CGC GGC ATC CTC AGC ATG GCC AAC TCC TGT GCC AAC AGC   1217
His Thr Gly Arg Gly Ile Leu Ser Met Ala Asn Ser Cys Ala Asn Ser
360                 365                 370                 375

AAC AGG TCT CAA TTC ATC ACG TTT CGC GTT GGG GGC TTT GAC TAC CTG GAC   1265
Asn Arg Ser Gln Phe Ile Thr Phe Arg Val Gly Gly Phe Asp Tyr Leu Asp
            380                 385                 390

AAG CAT ACC ATC TTT GGA CGG GTT GTG GGG GGT TTT GAC GTA CTG       1313
Lys His Thr Ile Phe Gly Arg Val Val Gly Gly Phe Asp Val Leu
        395                 400                 405

ACA GCC ATG GAG AAT GTG GAG AGT GAG CCC AAA ACT GAC CGC CCT AAG   1361
Thr Ala Met Glu Asn Val Glu Ser Asp Pro Lys Thr Asp Arg Pro Lys
410                 415                 420
```

FIG._2C

```
GAG GAG ATC CGC ATT GAT GCC ACT ACA GTG TTC GTG GAC CCC TAT GAG     1409
Glu Glu Ile Arg Ile Asp Ala Thr Thr Val Phe Val Asp Pro Tyr Glu
425                 430                 435

GAG GCC GAT GCC ATT GCG ATT GCG CAG GAG CGG ACA AAG CTC AAG GTA     1457
Glu Ala Asp Ala Ile Ala Ile Ala Gln Glu Arg Thr Lys Leu Lys Val
        440                 445                 450             455

GCC CCG GAG ACC AAA GTG AAG AGC CAG CAG GCA GGG AGC CAG             1505
Ala Pro Glu Thr Lys Val Lys Ser Gln Gln Pro Gln Ala Gly Ser Gln
        460                 465                 470

GGC CCC CAG ACC TTC CGC CAG GGC GTG GTG AAG TAC CTC AAC CCA GCA     1553
Gly Pro Gln Thr Phe Arg Gln Gly Val Val Lys Tyr Ile Asn Pro Ala
    475                 480                 485

GCC ACG AAG CGA GCA GCA GAG GAA GAG CCC TCA ACC AGT GCC ACT GTC     1601
Ala Thr Lys Arg Ala Ala Glu Glu Glu Pro Ser Thr Ser Ala Thr Val
490                 495                 500

CCC ATG TCC AAG AAG AAG CCC AGT CGG GGT TTT GGG GAC TTC AGC TCC     1649
Pro Met Ser Lys Lys Lys Pro Ser Arg Gly Phe Gly Asp Phe Ser Ser
505                 510                 515

TGG TAGCAGCAGG TTGGCCGCTG TGGACCTTGG TGGGGTTGCA GGGCTGGGGG          1702
Trp ...
520

CCCATGTCCA CATCTCCATT TCCAGCCTTT CTAGCCTGCC CTCTGCTGCC AGCCAATAAA   1762

TTGCTTGCCT GCTGCCTGCA TCCCCTTTCC TGGCCCCTGG GAGCCCACAG CCTTCCCATC   1822

CCTTAACCTG TTGCCAAGGG CCTTGGCCCT GTTTCCAGGA CCTGGCCCAG CCAGAGCCCA   1882
```

```
CTGCTGGGAC CTTCAAGCAC AAGGCCTGCC CTACACCCAG GCTGGTGCCT CAGGCCTCTC   1942
CTCTAGTAGG CAGGCCAGGT TAGTGAGGAA GGACTGTGTC TCCAGATTGT GGTTTCCTCT   2002
TTAAGACAGG GTCTTGCTCT GTTACCCAGG CTCCAGTGCA GTGGTGTGAT CATGGCTCAC   2062
TGCAGCCTCG ACCTCCTGGG CTCAAGCAAT CCTCCTGCCT CAGCCTCGCA AGTAGCTGGG   2122
ACTACAGCCG TGCACCACTA CATCCAGCTG TATATGTCTG GTTTTCTTAC CCCTACTTCT   2182
GTCATCTTCT CAGGGACAGC CTATTTATAC AACCAGTGTG GTCCCCTGAC CAACGCCATT   2242
ACCTGGGACA AGTTTTCAGA CCCCAGACTT ACTGAGCCTA AGCCTCTGCA GGGTGGGCTT   2302
CTCGGTCTGT TTTGACAAAA CTTTCAGGGC TTCTGAAGGC TGGTGTTGGA CGGCAGCATT   2362
GAGTTTCCTG CCGTGCCCTG CCTGAGCTCT CAGGGCCCTG GCGTCTCTGT CTGGCTGTGA   2422
ACCACCTGGG CTTCATCTCA AGCCTGCCTG GCCCCTGTGA GAATCTTGAG   2482
GGGACCCACA CTGGGTTGAG GCCAGTGTCT CCTGCTGTGA GAACAAGTGG ATGTCCCTCT   2542
CCCCGCCCCTC CTGCTGAAGT GGCCTTGCTG CTCTCAGGCC CGGCCAG                2589
```

FIG. 3A

```
           hCyP-60    1  MGKRQHQKDKMYITCAEYTHFYGGKKPD----LPQTNFRRLPFD HCSLSLQPFVYPVC TP
         CEF59E10_1   1  ···K······L·L·TS·WKSI-···H·D·TGTR·QRAQ·K····IN······L··ED···AR

57  DGIVFDLLNIVPWLKKYGTNPSNGEKLDGRSLIKLNFSKNSEGKY HCPVLFTVFTNNTHI
                     60  S·EI···TA···Y····H·K···CT·KP·VAKD··H·K·D·GED··FR···T·RT··DHS··

117  VAVRTTGNVYAYEAVEQLNIKAKNFRDLLTDEPFSRQDIITLQDPTNLDKFNVSNFYHVK
                    120  L·IA·S·····SH···QE··L·RNHLK·····v··T·A···D····NH·E····MEQ·L···

177  NNMKIIDPDE-EK-AKQDPSYYLKNTNAETRETLQELYKEFKGDEILAATMKAPEKKKVD
                    180  LDL·TSEEIKK··D·MK··KF·IRRM·NACKSV·DQ·D··YVPKKSSTE·D----TA---

235  KLNAAHYSTGKVSASFTSTAMVPETTHEAAAIDEDVLRYQFVKKKGYVRLHTNKGDLNLE
                    235  EI·········Q····A·G····V·A·V·SNK···VL·N·TV···SR····NAF····V··F·P····

295  LHCDLTPKTCENFIRLCKKHYYDGTIFHRSIRNFVIQGGDPTGTGTGGESYWGKPFKDEF
                    295  ·FAPKV··A······TH·SNG···NN··K····L·K···ML······H·····I·D···S···

355  RPNLSHTGRGILSMANSGPNSNRSQFFITFRSCAYLDKKHTIFGRVVGGFDVLTAMENVE
                    355  ISGF···DA··V·····K·S·T·G·····K····P·K····R·····L···Q·T··TI·KL·

415  SDPKTDRPKEEIRIDATTVFVDPYEEADAQIAQER-----KTQ-----L--KVAPETKVK
                    415  TEEG···V·MVSVV·MRAE·····F····EKEVQA··AEILK··SKDAAS··AN·K·K··AT·

463  SSQPQAGSQGPQTFRQGVGKYINPAA--TKRA--AEEEPSTSATVPMSKKKPSR-GFGDF
                    475  ---·E·V-------·······MKS··AVN··QGKM·DV·LEA·K----·T·FA·A·L···

518  SSW
                    521  ·K·
```

FIG._3C

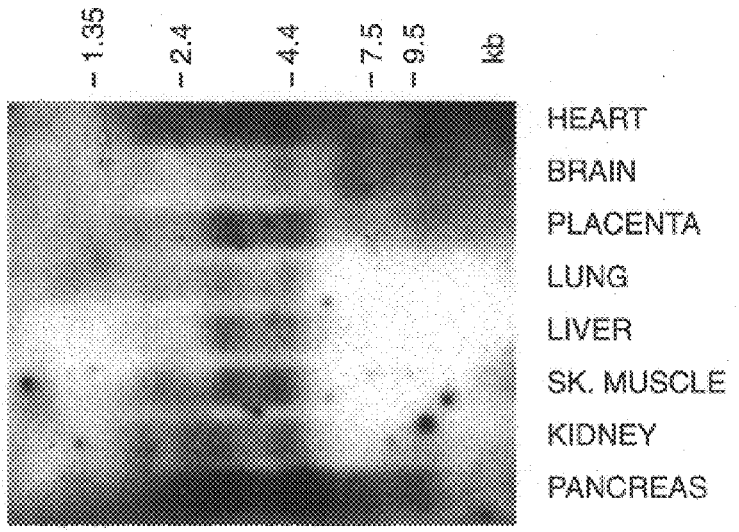
*FIG._4A*
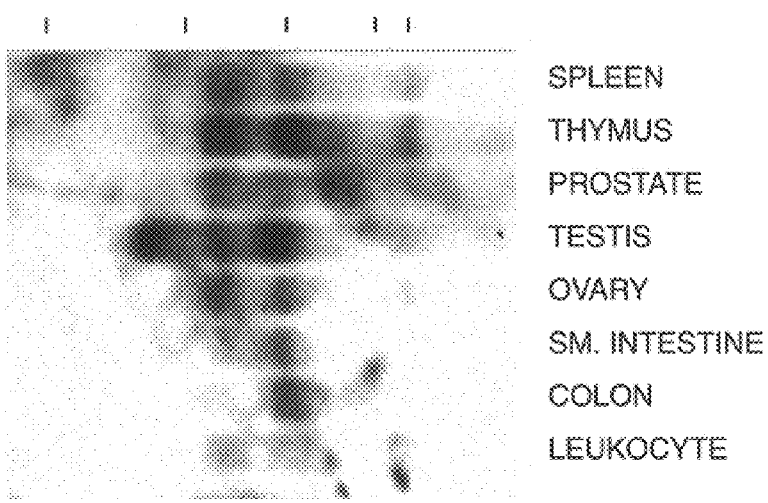
*FIG._4B*
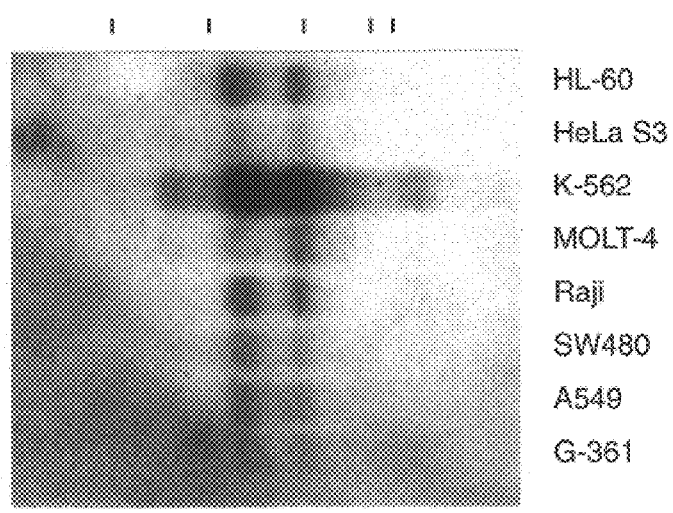
*FIG._4C*

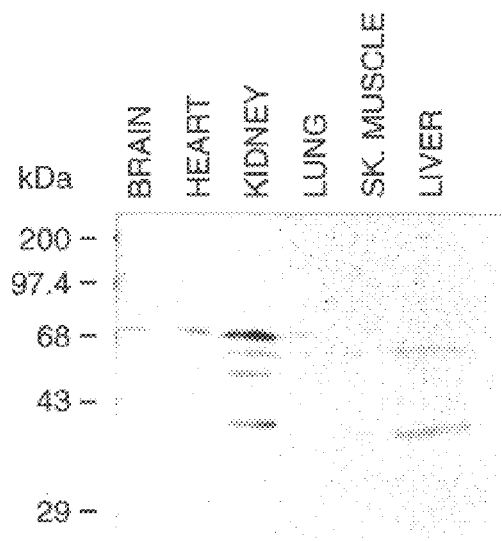
FIG._5A
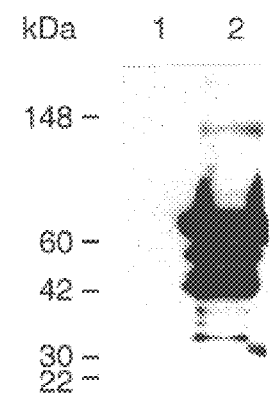
FIG._5B
| | |
|---|---|
| BLADDER | – |
| BRAIN | – |
| TONGUE | – |
| LUNG | –/+ |
| OVARY | –/+ |
| BREAST | + |
| HEART | + |
| LIVER | + |
| ADRENAL | ++ |
| PLACENTA | ++ |
| PROSTATE | ++ |
| SPLEEN | ++ |
| UTERUS | ++ |
| COLON | +++ |
| ENDOMETRIUM | +++ |
| KIDNEY | +++ |
| PANCREAS | +++ |
| STOMACH | +++ |
| TESTIS | +++ |
| THYROID | +++ |
| LYMPH NODE | ++++ |
FIG._7K

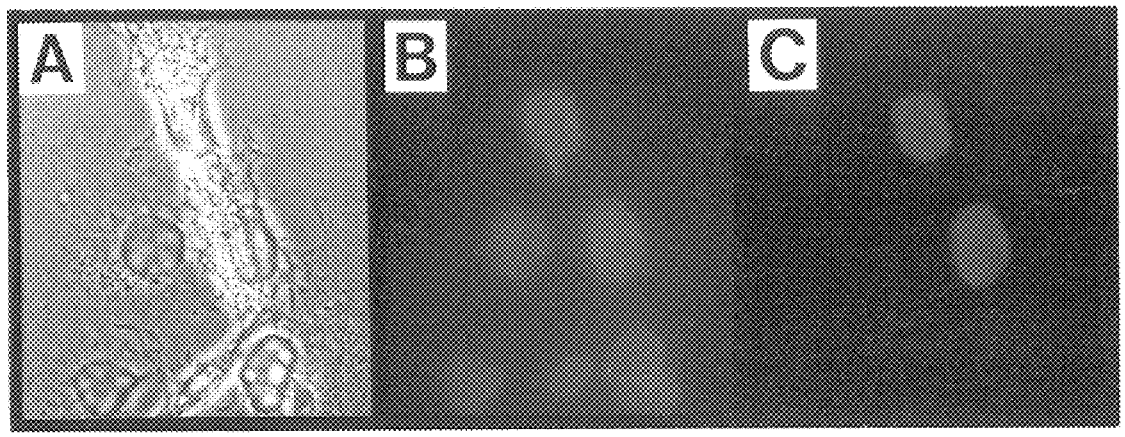
FIG._6A  FIG._6B  FIG._6C
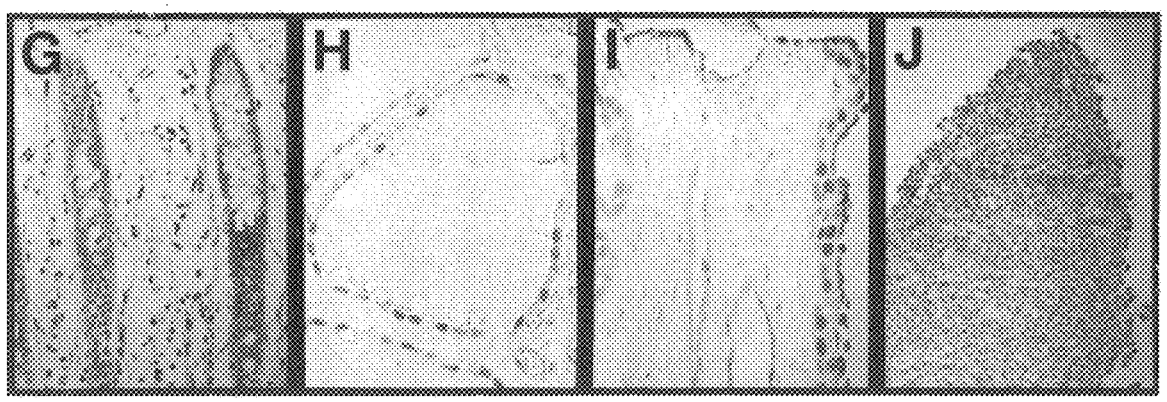
FIG._7G  FIG._7H  FIG._7I  FIG._7J

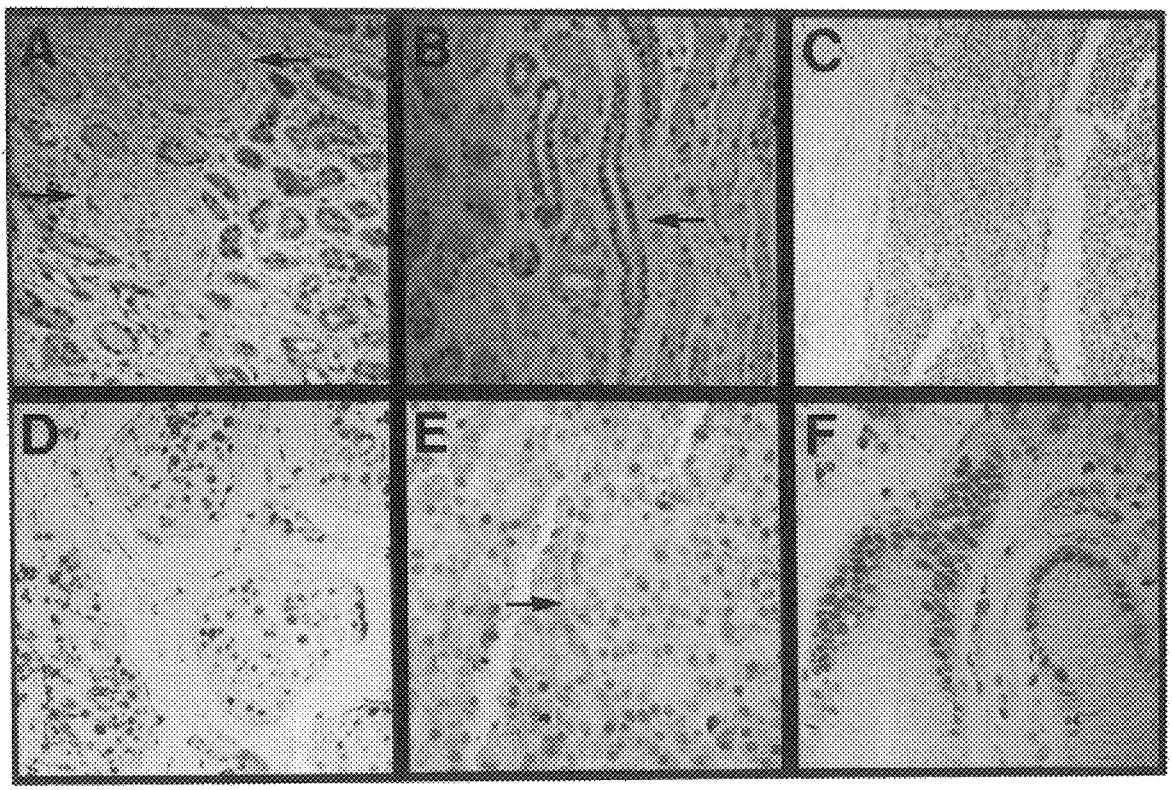
FIG._7A  FIG._7B  FIG._7C
FIG._7D  FIG._7E  FIG._7F

FIG._8A

| | | | | | |
|---|---|---|---|---|---|
| CAGCAGGCTG | CCTGATGACC | ACTAGAGGTA | TGTCTGCCCC | TCGTCACCCT | GCTGCACACC | 60
| AATCTGTGGC | CCTTCATCAT | GCTAAGAACA | AGAACTGCGC | CATGGCTGGC | TCCTTCTCTT | 120
| CTCCAGCCCA | TCCCTCTGCA | GCCTGTCATC | CCTGTCTGTG | ACCATTGGTC | GGGCCCCTGG | 180
| GCTCTAGAGT | GACTTTTGAC | GCCCTCCATC | CCTCCCGCCA | GGCACTGTCC | TCCGCAAGGC | 240
| CTGGTGCAGC | CCTGGCAGTA | ACTGGCTTGT | AAGAGGCTCA | GACACCAAGC | TGGGCCTGCA | 300
| GAGGAGGGGC | ACAGTAGGAC | ACAGTGACTG | CCCAGGTGTC | CACACACCTG | TAGGCCTCTG | 360
| AGCCAGCGTC | CAGGGTACAG | ATGCGGGTGG | TGGGGATGAA | GGCCTGACCA | GGGAGGGAGA | 420
| AGCAGGTTTG | GAGAGGACCC | TGTGCCCACC | CTGACAGACA | CCCTGGCTGG | CCCTGACTGA | 480
| CTGTATTCTC | TGGCCACATT | CAAGTCCCCC | ATTGGTGGGG | GCAGAGAAGT | AGGACCAGGC | 540
| CGTCCTTGGC | TCCAGAGCTC | GAAGACCCCA | AGACAGCCCT | CTGCTCTCAG | CGGCGCCACA | 600
| GAGAGCCTGG | GCTCAGCCTT | CTGCATCAGG | ACATGGCCTC | GTCCACTGAG | GGCACGATTT | 660
| AAACATTTGA | CATCAGAAGC | TTTATTTGTA | AACCTCACAC | AGATAAGGAC | CAAGGGCTGG | 720
| CGGTGTGGCC | AGAGGACAGG | GGAAGCTGAA | GGCCCCGTGC | TTGAGCTCGG | CAGTCCTGCT | 780
| CCTTGCAGTG | AAGCCACCAT | GGGTGACCGT | CCAGCCTCAC | CCGGTGGCCT | GCACAGTGAG | 840
| GGAAGGGCTT | CAGGGCCATC | TGCTCCCAGG | GCAGGGGACA | GGCCACCAAG | GACCTTTGGC | 900
| AAATGAAGGT | TTACATTTCT | GTAGTTTGTT | TGTTTTAGAG | CTTAATTTGT | AGTTTTTTAG | 960
| CTATTAAAAC | CATTTGAATT | TTTAACGACC | TGAGGCATCA | GGTAAATTAA | AGGATTTTGA | 1020

```
CAGCAGCAAC TTGCAGGCTG TACCTCTGCC CTTCCTTTTC TCATCAATCA CTGATGCTGA    60
AGCTGCAGGC CTGAGCCCTT TGTCTCCCTG GATGCTGGGT GGCGCCTCAT CTGCATCTCT   120
GCCTCACCCC ATCCACTGCC ACAGGCTGCC TGATGACCAC TAGAGGTATG TCTGCCCCTC   180
GTCACCCTGC TGCACACCAA TCTGTGGCCC TTCATCATGC TAAGAACAAG AACTGCGCCA   240
TGGCTGGCTC CTTCTCTTCT CCAGCCCATC CCTCTGCAGC CTGTCATCCC TGTCTGTGAC   300
CATTGGTCGG GCCCCTGGGC TCTAGAGTGA CTTTTGACGC CCTCCATCCC TCCCGCCAGG   360
CACTGTCCTC CGCAAGGCCT GGTGCAGCCC TGGCAGTAAC TGGCTTGTAA GAGGCTCAGA   420
CACCAAGCTG GGCCTGCAGA GGAGGGGCAC AGTAGGACAC AGTGACTGCC CAGGTGTCCA   480
CACACCTGTA GGCCTCTGAG CCAGCGTCCA GGGTACAGGT GCGGGTGGTG GGGATGAAGG   540
CCTGACCAGG GAGTGAGAAG CAGGTTTGGA GAGGACCCTG TGCCCACCCT GACAGACACC   600
CTGGCTGGCC CTGACTGACT GTATTCTCTG GCCACATTCA AGTCCCCCAT TGGTGGGGGC   660
AGAGAAGTAG GACCAGGCCA TCCTTGGCTA CAGAGCTCGA AGACCCCAAG ACAGCCCTCT   720
GCTCTCAGCG GCGCCACAGA GAGCCTGGGC TCAGCCTTCT GCATCAGGAC ATGGCCTCGT   780
CCACTGAGGG CACGATTTAA ACATTTGACA TCAGAAGCTT TATTTGTAAA CCTCACACAG   840
ATAAGGACCA AGGGCTGGCG GTGTGGCCAG AGGACAGGGG AAGCTGAAGG CCCCGTGCTT   900
GAGCTCGGCA GTCCTGCTCC TTGCAGTGAA GCCACCATGG GTGACCGTCC AGCCTCACCC   960
GGTGGCCTGC ACAGTGAGGG AAGGGCTTCA GGGCCATCTG CTCCCAGGGC AGGGGACAGG  1020
CCACCAAGGA CCTTTGGCAA ATGAAGGTTT ACATTTCTGT AGTTTGTTTG TTTTAGAGCT  1080
TAATTTGTAG TTTTTTAGCT ATTAAAACCA TTTGAATTTT TA                    1122
```

NUCLEAR CYCLOPHILIN

FIELD OF THE INVENTION

The invention relates generally to a novel nuclear cyclophilin.

BACKGROUND OF THE INVENTION

The immunophilins are a class of molecules implicated in a variety of functions, most notably immunoregulation. Immunophilins are the protein receptors for the potent immunosuppressive drugs cyclosporin A, FK506, and rapamycin. These drugs are used to prevent graft rejection and to treat autoimmune disorders. There are two major classes of these immunophilins: the cyclosporin A binding proteins, designated cyclophilins, and the FK506 binding proteins (FKBPs). Although they have related functions, these two groups lack structural and sequence homology.

The cyclophilin/cyclosporin A complex and the FKBP/FK506 complex apparently accomplish immunosuppression by blocking the Ca+2/calmodulin-dependent serine/threonine protein phosphatase activity of calcineurin, an enzyme that supposedly plays a role in the signal transduction pathway leading to translocation of certain transcription factors from the cytosol to the nucleus of mammalian T cells. Inhibition of the phosphatase activity of calcineurin appears to block T cell activation and inhibits T cell lymphokine production. Specifically, cyclosporin A and FK506 inhibit expression of IL-2, IL-3, IL-4, GM-CSF, TNF-alpha, gamma-interferon, and other nonlymphokine genes (e.g. IL-2R). Rapamycin is structurally similar to FK506 but suppresses T cell activation at a different level, mainly through inhibition of proliferation induced by lymphokines.

In addition to their immunosuppressive functions, the immunophilins have peptidyl-prolyl cis-trans isomerase activity (also sometimes referred to as rotamase activity). This activity is putatively unrelated to immunosuppression. Additionally, there is some suggestion that the immunophilins can act as an ATP-independent chaperone protein, facilitating the folding of target proteins and the assembly of multisubunit protein complexes (see Price et al., Proc. Natl. Acad. Sci. 91:3931 (1994); Freskgard et al., Science 258:466 (1992)), although this activity is unclear (Kern et al., FEBS Letters 348:145 (1994)).

The cyclophilins are apparently ubiquitous throughout nature, and the sequences of more than 27 cyclophilins and 17 FKBPs are known. Sequence alignment of the cyclophilin sequences reveals two "signature" sequences which are present in almost all of the cyclophilins (see Trandinh et al., FASEB J. 6:3410 (1992). In addition, the position corresponding to residue 121 in human cyclophilin A has been implicated in strong cyclosporin binding (see Liu et al., Biochem. 30:2306–2310 (1991)). The E. coli cyclophilins, which bind poorly to cyclosporin, have a phenylalanine at this position; when this residue is mutated to tryptophan, the isomerase activity becomes more sensitive to cyclosporin.

Finally, only a few of the native cyclophilin substrates are known, most notably Drosophila rhodopsin and HIV-1 Gag (see Luban et al., Cell 73:1067–78 (1993); Stamnes et al., Cell 65:219–227 (1991)). Accordingly, the actual mechanisms and processes by which the cyclophilins effect their regulatory mechanisms are not yet elucidated.

SUMMARY OF THE INVENTION

It is an object of the present invention to provide a novel nuclear cyclophilin.

Accordingly, the present invention provides recombinant cyclophilin-60 proteins, and isolated or recombinant nucleic acids which encode the cyclophilin-60 proteins of the present invention. Also provided are expression vectors which comprise nucleic acid encoding a cyclophilin-60 protein operably linked to transcriptional and translational regulatory nucleic acid, and host cells which contain the expression vectors.

An additional aspect of the present invention provides methods for producing cyclophilin-60 proteins which comprise culturing a host cell transformed with an expression vector and causing expression of the nucleic acid encoding the cyclophilin-60 protein to produce a recombinant cyclophilin-60 protein.

An additional aspect provides monoclonal antibodies to the cyclophilin-60 proteins of the present invention.

BRIEF DESCRIPTION OF THE DRAWINGS

FIGS. 1A and 1B describe the results of the yeast two-hybrid system. The yeast two-hybrid system is a genetic assay (Fields and Song, Nature 340:245–246 (1989) designed to detect protein-protein interactions in vivo. The assay is based on the fact that the DNA-binding and transcriptional activation domains of GAL4 are separable domains. The "bait" or target protein "X" is fused to the GAL4 DNA-binding domain and is localized in the nucleus to a specific promoter upstream of a reporter gene such as beta-galactosidase. A cDNA library composed of sequences "Y" fused to the GAL4 activation domain is co-expressed with the "bait" protein. Interacting proteins "X+Y" allow transcriptional activation of the reporter gene. FIG. 1A depicts a schematic representation of the GAL4 DNA binding domain/eglin M2 Flag fusion protein (pBDeglin) and the B lymphocyte library GAL4 activation domain fusions. The DNA binding domain contains residues 1–147 of the GAL4. The P3 to P3' residues in the binding loop of eglin (SEQ ID NO:1) are indicated (Val 43 to Arg 48). A Pro at residue 42 is also exposed in the binding loop. The M2 Flag epitope (SEQ ID NO:2) is indicated. The GAL4 activation domain contains residues 768–881. The average insert size in the B lymphocyte library was 1.7 kb. (B) is a table showing the specific interaction of eglin c and the cyclophilin-60 protein. Yeast strain HF7c was transformed with the above combinations of plasmids and the resulting colonies were assayed for beta-galactosidase activity. White colonies indicate the absence of activity or an interaction, while blue colonies indicate the presence of activity or an interaction. pBDeglin, binding domain/eglin hybrid plasmid; pGBT9, binding domain plasmid; pVA3, binding domain/p53 hybrid plasmid; pTD1, activation domain/SV40 large T antigen hybrid plasmid; pAD16.1, activation domain/16.1 hybrid plasmid.

FIG. 2 depicts the nucleotide and predicted amino acid sequence of cyclophilin-60 (SEQ ID NOS:3 and 4). The cDNA sequence shown is from clone 6.1. Two additional clones (pAD16.1 and 26.1) were partially overlapping and had different 3' untranslated regions. The region with homology to other known cyclophilins is underlined. Asterisks indicate the stop codon. Boxed residues may represent nuclear localization motifs. Circled residues represent potential phosphorylation sites. The filled circle indicates the position where the cDNA was fused to the GAL4 activation domain in pAD16.1. The arrow shows the position where the M2 Flag epitope (DYKDDDDK) (SEQ ID NO:2) was inserted. Although the cDNA pAD16.1 is not full length, it is likely that the beginning of the protein is contained within the clone because of an in-frame stop codon 54 bp upstream of the first ATG. Amino acid residues are numbered on the left and the cDNA basepairs are numbered on the right.

FIGS. 3A (SEQ ID NOS:5 and 16) and 3B depict the comparison of cyclophilin-60 with other known cyclophilins. (A) Cyclophilins with the highest level of identity from *C. elegans*, human, Drosophila, and *S. cerevisiae* are compared to cyclophilin-60 (SEQ ID NO:5). All other human cyclophilins are shown for comparison. Asterisks indicate identity. Gaps (dashes) were inserted to maximize the homology. Numbers indicate the residue position. The arrow indicates the Trp residue important for cyclosporin binding. Two "signature" sequences are underlined. The first consensus sequence is (G/A)X(L/I/V)X(L/I/V/M/F)X(L/T) XXXXXP(K/E/V)(T/S)(A/V)XNF (SEQ ID NO:17). The second consensus sequence is (Y/F)X(G/N)(S/T/V)XFHR (I/V)(I/V)XXF(M/L)(L/I/V/C)Q(G/A)G(D/G) (SEQ ID NO:18) (Trandinh et al., FASEB 6:3410 (1992)). The human ORF (residues 623–644) is also 50% identical to cyclophilin-60 (residues 412–433; data not shown). With the exception of the *C. elegans* cyclophilin and human ORF, no additional similarities outside this domain were detected. (B) Table depicting the percentage identity in the region shown in (A). FIG. 3C: The *C. elegans* cyclophilin-like gene CEF59E10_1 (SEQ ID NO:19) is compared to cyclophilin-60 (SEQ ID NO:4). Boxed residues depict 2 repeats which may represent a structural motif of unknown function. Asterisks indicate identity and dashes indicate gaps. Sequence comparisons were performed using the blastp program (National Center for Biotechnology Information), SeqEd v1.0.3 (Applied Biosystems) and by visual inspection.

FIGS. 4A, 4B and 4C depict the expression of cyclophilin-60 mRNA in human tissues and cell lines. Multiple tissue and cancer cell line Northern blots were probed with either of two fragments of the cyclophilin-60 cDNA as described (Clontech). Fragment 1 was basepairs 719–1260; fragment 2 was basepairs 173–1178. Sk. muscle= skeletal muscle; sm. intestine=small intestine, leukocyte= peripheral blood leukocyte.

FIGS. 5A and 5B show that cyclophilin-60 is found in various tissues. (A) A multiple tissue western blot was probed with affinity-purified anti-cyclophilin-60 antiserum. Approximately 75 micrograms of total protein per lane was fractionated on a 15% SDS-PAGE gel (Clontech). No bands were seen when the same blot was stripped and reprobed with secondary antibody only. Sk muscle=skeletal muscle. (B) Western blot of COS-7 cell lysates from untransfected cells (lane 1) or cells transiently transfected with an cyclophilin-60-Flag cDNA construct (lane 2). Proteins were fractionated on a 4–20% SDS-PAGE gel, transferred to nitrocellulose, and probed with the M2 monoclonal antibody.

FIG. 6, panels A, B, and C depict the localization of cyclophilin-60 to the nucleus. (A) Standard light microscopy of COS-7 cells transiently transfected with an cyclophilin-60-Flag cDNA construct. (B) Nuclear staining of cells shown in (A) with Hoechst dye. (C) Nuclear staining of cells shown in (A) with the M2 monoclonal and rhodamine-labelled goat anti-mouse secondary antibodies. Untransfected cells show no staining (data not shown).

FIGS. 7A–7J depict the immunohistological localization of cyclophilin-60 in various human tissues. (A) kidney: arrows indicate glomeruli; (B) kidney: arrow indicates collecting duct; (C) lymph node; (D) testis; (E) pancreas, arrow indicates an islet of Langerhaus; (F) stomach; (G) colon; (H) thyroid; (I) prostate; (J) squamous cell carcinoma; (K) overall staining intensity: –none, +weak, ++moderate, +++strong, few cells; ++++strong, many cells.

FIGS. 8A and 8B depict the 3' untranslated region (UTR) of two additional cyclophilin-60 CDNA clones (SEQ ID NO:20 and 21). (A) Clone 26.1, basepairs 904–1928; (SEQ ID NO:20) the difference between the clones begins at basepair 910. (B) Clone pAD16.1, basepairs 939–2060; the difference begins at basepair 945. Clone 6.1 is shown in FIG. 2 (SEQ ID NO:3 and 4), and includes basepairs 1656–2589; the difference begins at 1662. The UTRs of 26.1 and pAD16.1 are very similar.

DETAILED DESCRIPTION OF THE INVENTION

The present invention provides novel cyclophilin-60 proteins. In a preferred embodiment, the cyclophilin-60 proteins are from humans. However, using the techniques outlined below, cyclophilin-60 proteins from other organisms may also be obtained.

Without being bound by theory, it appears that the cyclophilin-60 proteins of the invention weakly bind cyclosporin. In addition, the cyclophilin-60 proteins of the invention appear to be localized in the nucleus of the cell, as described below.

Frequently patients treated with cyclosporin to induce immunosuppression experience kidney toxicity. Interestingly, as shown in the Examples, the highest level of cyclophilin-60 expression was detected in kidney using cyclophilin-60 antibodies. In addition, FIG. 7 shows staining in kidney tubule cells, which are affected by cyclosporin toxicity. Thus, it is possible that a change in cyclophilin-60 levels or activity in the kidney due to cyclosporin binding contributes to kidney damage. Accordingly, the cyclophilin-60 proteins of the present invention are useful as targets for analyzing cyclosporin binding and tissue toxicity, targets for regulating cellular responses and regulating nuclear response/processes.

Lower levels were detected in brain, heart and lung tissue (FIG. 5A). High levels of cyclophilin-60 mRNA was also detected via Northern blots using cyclophilin-60 cDNA in pancreas, thymus, and testis with lower expression in brain and peripheral blood leukocytes.

A cyclophilin-60 protein may be identified and defined in several ways. In one embodiment, a cyclophilin-60 nucleic acid or cyclophilin-60 protein is initially identified by substantial nucleic acid and/or amino acid sequence homology to the sequences shown in FIG. 2 (SEQ ID NO:3 and 4). Such homology can be based upon the overall nucleic acid or amino acid sequence.

As used herein, a protein is a "cyclophilin-60 protein" if the overall homology of the protein sequence to the amino acid sequence shown in FIG. 2 (SEQ ID NO:4) is greater than about 70%, preferably greater than about 75% and more preferably greater than 85%. In some embodiments the homology will be as high as about 90 to 95 or 98%. This homology will be determined using standard techniques known in the art, such as the Best Fit sequence program described by Devereux et al, *Nucl Acid Res.* 12:387–395 (1984), the blastp program (National Center for Biotechnology Information) or SeqEd (Applied Biosystems). The alignment may include the introduction of gaps in the sequences to be aligned. In addition, for sequences which contain either more or fewer amino acids than the protein shown in FIG. 2 (SEQ ID NO:4), it is understood that the percentage of homology will be determined based on the number of homologous amino acids in relation to the total number of amino acids. Thus, for example, homology of sequences either longer or shorter than that shown in FIG. 2 (SEQ ID NO:3 and 4), as discussed below, will be determined using the number of amino acids in the shorter sequence as the total number of amino acids. In addition, in the preferred embodiment, homology is determined using identical versus similar residues.

Figure 3A:
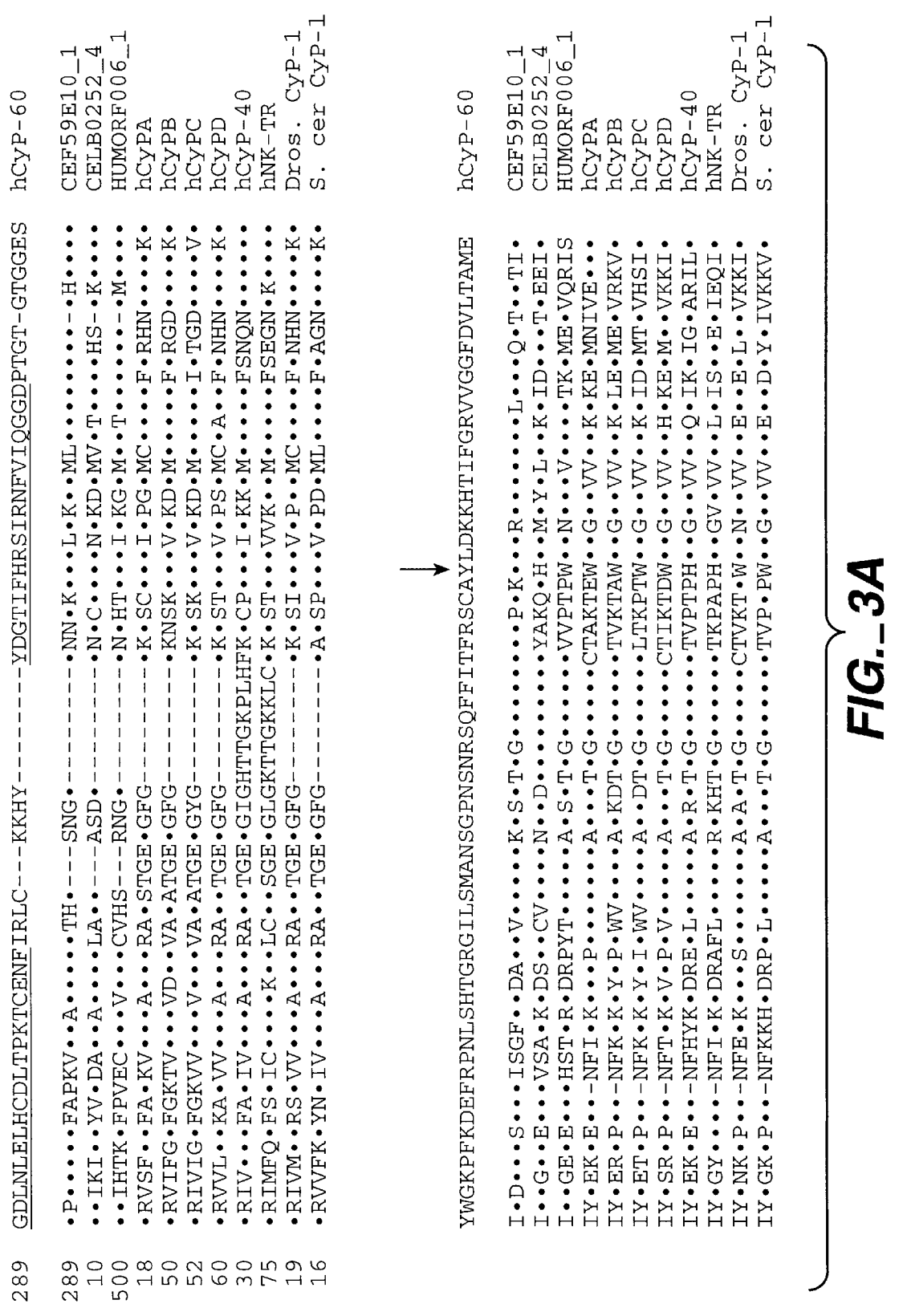

The cyclophilin-60 proteins of the present invention have limited sequence homology to other cyclophilins. The basis of this homology is found in the cyclophilin domains of cyclophilins produced by C. elegans, Drosophila, S. cerevisiae, and to a human open reading frame (ORF), (see FIG. 3B for Genbank Accession Numbers). The cyclophilin domain contains the two "signature" sequences of cyclophilins, indicated in FIG. 3A. On the amino acid level, the cyclophilin-60 protein has an overall 50% homology with the C. elegans protein (CEF59E10_1, Accession numbers Z36949/Z466935), with the homology in the cyclophilin domain being roughly 66%. As between the human ORF (HUMORF006_1 (SEQ ID NO:8), Accession number D38552) and cyclophilin-60, there is a 51% homology. The Drosophila and S. cerevisiae proteins have homology only in the cyclophilin domain. As between Drosophila (DrosCyP-1 (SEQ ID NO:15), accession number M62398) and cyclophilin-60, the cyclophilin-60 proteins are roughly 54% homologous in the cyclophilin domain, with the homology between S. cerevisiae (Cyp-1 (SEQ ID NO:16), accession number M30513) and cyclophilin-60 being roughly 50% in the cyclophilin domain.

Comparison of the cyclophilin-60 sequence (SEQ ID NO:4) to other sequences reveals that the amino- and carboxy-termini of the protein are unique; that is, residues 1 to 288 and residues 412–520 of the cyclophilin-60 protein (SEQ ID NO:4) have little or no homology to known human protein sequences. Accordingly, this amino-terminal sequence is particularly useful in identifying cyclophilin-60 proteins. Thus, a cyclophilin-60 protein may have low overall homology to the sequence depicted in FIG. 2 (SEQ ID NO:4) but contain the amino-terminal or carboxy-terminal sequence and thus be considered a cyclophilin-60 protein. Similarly, nucleic acid encoding this amino-terminal portion is particularly useful in probing other organisms for cyclophilin-60 sequences.

Cyclophilin-60 proteins of the present invention may be shorter or longer than the amino acid sequence shown in FIG. 2 (SEQ ID NO:4). In a preferred embodiment, included within the definition of cyclophilin-60 proteins, are portions or fragments of the sequence shown in FIG. 2 (SEQ ID NO:4). The fragments may range from about 50 to about 500 amino acids. Fragments of at least about 150 amino acids are preferred and fragments of at least about 400–500 amino acids are particularly preferred. A portion of the N-terminus, (e.g. from about 100 to about 200 of the N-terminal amino acids) may be removed during post-translational processing.

The fragments are identified as cyclophilin-60 proteins on the basis of homology and biological activity. Thus, a portion of the cyclophilin-60 protein is considered a cyclophilin-60 protein if it shares at least one epitope with the full length cyclophilin-60, as described below. Alternatively, the fragment may have biological activity such as rotamase activity, chaparonin activity, DNA, protein or enzyme binding activity, or immunoregulatory activity when bound to a cyclosporin or other regulatory molecule, among others.

In a preferred embodiment, when the cyclophilin-60 protein is to be used to generate antibodies, the cyclophilin-60 protein must share at least one epitope or determinant with the full length protein shown in FIG. 2. By "epitope" or "determinant" herein is meant a portion of a protein which will generate and bind an antibody. Thus, in most instances, antibodies made to a smaller cyclophilin-60 protein will be able to bind to the full length protein. In a preferred embodiment, the epitope is unique; that is, antibodies generated to a unique epitope show little or no cross-reactivity with other proteins.

In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence. Thus the homology of the nucleic acid sequence as compared to the nucleic acid sequences of FIG. 2 (SEQ ID NO:3) (that is, the depicted sequence and the inherent complement) is greater than about 60%, preferably greater than about 70% and more preferably greater than about 80%. In some embodiments the homology will be as high as about 90 to 95 or 98%.

As for the protein, the amino-terminal portion of the cyclophilin-60 nucleic acid is particularly useful for identifying cyclophilin-60 proteins. In particular, sequences homologous between cyclophilin-60 and the C. elegans proteins, (e.g. residues 1–10) are useful. In addition, carboxy-terminal sequences are also useful, e.g. residues 433–442.

The nucleic acid sequences encoding the cyclophilin-60 proteins have limited nucleic acid homology to cyclophilins from C. elegans, a human ORF, Drosophila, and S. cerevisiae. Specifically, the nucleic acid sequence encoding the protein from C. elegans has an overall 53% homology with the human cyclophilin-60 nucleic acid shown in FIG. 2 (SEQ ID NO:3). Similarly, as between Drosophila and cyclophilin-60, the homology is 57%, with the homology between S. cerevisiae and cyclophilin-60 being 54%. The homology between cyclophilin-60 and HUMORF006 (SEQ ID NO:8) is 51%.

In one embodiment, the nucleic acid homology is determined through hybridization studies. Thus, for example, nucleic acids which hybridize under high stringency to all or part of the nucleic acid sequence shown in FIG. 2 (SEQ ID NO:3), or its complement, are considered cyclophilin-60 protein genes.

High stringency conditions are generally 0.1×SSC at 65° C., although less stringent conditions may be used for unique probe sequences such as the amino-terminal portion of the gene. Less stringent conditions include 2×SSC at 25° C.

As it is understood by those in the art, once the amino acid sequence of cyclophilin-60 is known, it is possible to generate a large number of nucleic acids which code for the cyclophilin-60 amino acid sequence, due to the degeneracy of the genetic code. Thus, for example, synthetic oligonucleotides may be made which use different codons than the naturally occurring or native codons, and the synthetic oligonucleotides incorporated into the cyclophilin-60 nucleic acid using techniques well known in the art.

The cyclophilin-60 proteins and nucleic acids of the present invention are preferably recombinant. As used herein, "nucleic acid" may refer to either DNA or RNA, or molecules which contain both deoxy- and ribonucleotides.

The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments. Specifically included within the definition of nucleic acid are ribozyme and anti-sense nucleic acids. Generally, anti-sense nucleic acids function to prevent expression of mRNA, such that a cyclophilin-60 protein is not made. An anti-sense nucleic acid will hybridize to the nucleic acid sequences shown in FIG. 2 (SEQ ID NO:3) or their complements, but may contain ribonucleotides as well as deoxyribonucleotides. The hybridization conditions used for the determination of anti-sense hybridization will generally be high stringency conditions, such as 0.1×SSC at 65° C.

The nucleic acid may be double stranded, single stranded, or contain portions of both double stranded or single stranded sequence. By the term "recombinant nucleic acid" herein is meant nucleic acid, originally formed in vitro, in general, by the manipulation of nucleic acid by endonucleases, in a form not normally found in nature. Thus an isolated cyclophilin-60 protein nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated away from some or all of the proteins and compounds with which it is normally associated in its wild type host. The definition includes the production of a cyclophilin-60 protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions.

Also included with the definition of cyclophilin-60 protein are cyclophilin-60 proteins from other organisms, which are cloned and expressed as outlined below. The cyclophilin-60 protein sequences of FIG. 2 (SEQ ID NO:4) may be lined up with the C. elegans sequence, as is done in FIG. 3C (SEQ ID NOS:4 and 19), and homologous sequences may be selected for possible probe sequences, making degenerate oligonucleotides. In particular, the amino-terminal sequence from 1 to 10 may be used.

In a preferred embodiment, the cyclophilin-60 proteins of the present invention bind cyclosporin and other immunomodulators, including CsA-like molecules with varying affinities.

In a preferred embodiment, the cyclophilin-60 proteins of the present invention may bind proteases, enzymes and inhibitors. As outlined in the Examples, cyclophilin-60 proteins were first identified by their ability to bind the serine protease inhibitor eglin c (SEQ ID NO:1). Without being bound by theory, it appears that many protease inhibitors contain an exposed proline residue in the reactive site. Of the six proline residues in eglin c (SEQ ID NO:1), the proline at position 42 is particularly exposed in the binding loop, leading to the speculation that it is this residue which interacts with cyclophilin-60. The fact that cyclophilin-60 was identified via the interaction of eglin c suggests that cyclophilin-60 can be thought of as "protease-like".

Once the cyclophilin-60 protein nucleic acid is identified, it can be cloned and, if necessary, its constituent parts recombined to form the entire cyclophilin-60 protein nucleic acid. Once isolated from its natural source, e.g., contained within a plasmid or other vector or excised therefrom as a linear nucleic acid segment, the recombinant cyclophilin-60 protein nucleic acid can be further used as a probe to identify and isolate other cyclophilin-60 protein nucleic acids. It can also be used as a "precursor" nucleic acid to make modified or variant cyclophilin-60 protein nucleic acids and proteins.

Using the nucleic acids of the present invention which encode cyclophilin-60 protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the cyclophilin-60 protein. "Operably linked" in this context means that the transcriptional and translational regulatory DNA is positioned relative to the coding sequence of the cyclophilin-60 protein in such a manner that transcription is initiated. Generally, this will mean that the promoter and transcriptional initiation or start sequences are positioned 5' to the cyclophilin-60 protein coding region. The transcriptional and translational regulatory nucleic acid will generally be appropriate to the host cell used to express the cyclophilin-60 protein; for example, transcriptional and translational regulatory nucleic acid sequences from Bacillus are preferably used to express the cyclophilin-60 protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The cyclophilin-60 proteins of the present invention are produced by culturing a host cell transformed with an expression vector containing nucleic acid encoding a cyclophilin-60 protein, under the appropriate conditions to induce or cause expression of the cyclophilin-60 protein. The conditions appropriate for cyclophilin-60 protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli, Bacillus siibtilis,* SF9 cells, C129 cells, 293 cells, Neurospora, BHK, CHO, COS, and HeLa cells, immortalized mammalian myeloid, and lymphoid cell lines. In one embodiment, the genes are expressed in *C. elegans* strains with mutations in the homologous gene in complementation studies. Particularly preferred expression systems include *E. coli* and baculoviral systems.

In a preferred embodiment, cyclophilin-60 proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of cyclophilin-60 protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the cyclophilin-60 protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris,* and *Streptococcus lividans,* among others.

The bacterial expression vectors are transformed into bacterial host cells using techniques well known in the art, such as calcium chloride treatment, electroporation, and others.

In one embodiment, cyclophilin-60 proteins are produced in insect cells. Expression vectors for the transformation of insect cells, and in particular, baculovirus-based expression vectors, are well known in the art.

Mammalian expression systems are also known in the art and are used in one embodiment. A mammalian promoter is any DNA sequence capable of binding mammalian RNA polymerase and initiating the downstream (3') transcription of a coding sequence for cyclophilin-60 protein into mRNA. A promoter will have a transcription initiating region, which is usually place proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element, typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, and herpes simplex virus promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, encapsulation of the polynucleotide (s) in liposomes, and direct microinjection of the DNA into nuclei.

In a preferred embodiment, stably transfected mammalian cell lines which express cyclophilin-60 are made, as is depicted in the examples.

In a preferred embodiment, cyclophilin-60 protein is produced in yeast cells. Yeast expression systems are well known in the art, and include expression vectors for *Sac-*

*charomyces cerevisiae, Candida albicans* and *C. maltosa, Hansenula polymorpha, Kluyveromyces fragilis* and *K. lactis, Pichia guillerimondii* and *P. pastoris, Schizosaccharomvces pombe,* and *Yarrowia lipolytica.* Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the G418 resistance gene, which confers resistance to G418; and the CUP1 gene, which allows yeast to grow in the presence of copper ions.

A recombinant cyclophilin-60 protein may be expressed intracellularly or secreted.

The cyclophilin-60 protein may also be made as a fusion protein, using techniques well known in the art. Thus, for example, for the creation of monoclonal antibodies, if the desired epitope is small, the cyclophilin-60 protein may be fused to a carrier protein to form an immunogen. Alternatively, the cyclophilin-60 protein may be made as a fusion protein to increase expression.

Also included within the definition of cyclophilin-60 proteins of the present invention are amino acid sequence variants. These variants fall into one or more of three classes: substitutional, insertional or deletional variants. These variants ordinarily are prepared by site specific mutagenesis of nucleotides in the DNA encoding the cyclophilin-60 protein, using cassette mutagenesis or other techniques well known in the art, to produce DNA encoding the variant, and thereafter expressing the DNA in recombinant cell culture as outlined above. However, variant cyclophilin-60 protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the cyclophilin-60 protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed cyclophilin-60 protein variants screened for the optimal combination of desired activity. Techniques for making substitution mutations at predetermined sites in DNA having a known sequence are well known, for example, M13 primer mutagenesis. Screening of the mutants is done using assays of cyclophilin-60 protein activities. For example, the isomerase activity may be evaluated, using techniques well known in the art (see Fischer et al., Biomed. Biochim. Acta 43:1101–11 (1984); Harrison et al., Biochem. 29:1684–1689 (1990)). Cyclosporin A or other immunoregulator binding may be measured. Similarly, mutated cyclophilin-60 nucleic acids are placed in cyclophilin-60 deletion strains and tested for cyclophilin-60 activity. The creation of deletion strains, given a gene sequence, is known in the art.

Amino acid substitutions are typically of single residues; insertions usually will be on the order of from about 1 to 20 amino acids, although considerably larger insertions may be tolerated. Deletions range from about 1 to 30 residues, although in some cases deletions may be much larger, as for example when one of the domains of the cyclophilin-60 protein is deleted.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the cyclophilin-60 protein are desired, substitutions are generally made in accordance with the following chart:

Chart I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the cyclophilin-60 proteins as needed. Alternatively, the variant may be designed such that the biological activity of the cyclophilin-60 protein is altered. For example, the tyrosine at position 389 of the sequence of FIG. 2 may be altered. This residue corresponds to tryptophan 121 in human cyclophilin A and has been implicated in strong cyclosporin binding. *E. coli* cyclophilins bind poorly to cyclosporin and have a phenylalanine at this position. Interestingly, both the *C. elegans* and cyclophilin-60 proteins have a tyrosine at this position. Thus, this amino acid may be substituted with a tryptophan, histidine or phenylalanine. Additionally, the putative protein kinase A sequence at position 283, putative protein kinase C sequences at positions 323 and 418, and glycogen synthase kinase-3 phosphorylation sites at positions 55, 243, 300, 340, 367, 371, 459 and 502 may be altered. Furthermore, there are three triplets of lysine residues at positions 230–232, 277–279 and 507–509, and lysine/arginine residues at 490–491 which may represent nuclear localization sequences which may be altered.

In addition, the putative residues involved in isomerase activity and/or cyclosporin binding may be altered. The residues of human cyclophilin A which have been shown to contact cyclosporin A (CsA) are Lys31, Arg55, Gln63, Glu81, Asn102, Trp121 and His126. Thus, residues of cyclophilin-60 which correspond to or are equivalent to these cyclophilln-A residues may be altered. By "corresponding to" or "equivalent positions" herein is meant amino acid positions which may be determined by lining up the two sequences and determining the equivalent position in the other protein, as is well known in the art.

In a preferred embodiment, the cyclophilin-60 protein is purified or isolated after expression. Cyclophilin-60 proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the cyclophilin-60 protein may be purified using a standard aniti- cyclophilin-60 antibody column. Ultrafiltration and diafiltration techniques, in conjunction with protein concentration, are also useful. For general guidance in suitable purification techniques, see Scopes, R., Protein Purification, Springer-Verlag, N.Y. (1982). The degree of purification necessary will vary depending on the use of the cyclophilin-60 protein. In some instances no purification will be necessary.

Once expressed and purified if necessary, the cyclophilin-60 proteins are useful in a number of applications.

For example, the cyclophilin-60 proteins can be coupled, using standard technology, to affinity chromatography columns. These columns may then be used to purify antibodies to cyclophilin-60. The purified antibodies may then be used as outlined below.

Due to the role of cyclosporin in kidney damage and toxicity, the identification of high levels of cyclophilin-60 in the kidney, and the localization in kidney cells affected by CsA, full length cyclophilin-60 proteins or fragments of cyclophilin-60 proteins are also useful in diagnostic assays for the presence of cyclophilin-60 proteins in the tissues, such as kidney. These assays include as radioimmunoassays, which use both cyclophilin-60 protein antibodies and cyclophilin-60 proteins. For example, competitive inhibition, direct RIA, and sandwich RIA assays are well known in the art.

The cyclophilin-60 proteins of the present invention, may also be used to screen drugs which either inhibit or enhance the biological function of cyclophilin-60. Thus, the cyclophilin-60 proteins may be used as drug targets. Alternatively, the proteins may be used as an "anti-target" for drugs which affect immunosuppression but which do not affect the biological function of cyclophilin-60. For example, since kidney toxicity may be related to cyclophilin-60, it may be desirable to screen for drugs which bind to other cyclophilins for immunosuppression but do not bind cyclophilin-60.

In a preferred embodiment, the cyclophilin-60 proteins are expressed in bacterial systems and used for drug screening, as is well known in the art.

Additionally, the cyclophilin-60 proteins are useful to make antibodies to cyclophilin-60 proteins. These antibodies find use in a number of applications, including diagnostic assays for the presence of cyclophilin-60 in different tissues or samples, such as kidney or urine, and during treatment with cyclophilin-60 binding drugs such as cyclosporins.

In a preferred embodiment, polyclonal and monoclonal antibodies are generated to the cyclophilin-60 protein, using techniques well known in the art. As outlined above, the antibodies may be generated to the full length cyclophilin-60 protein, or a portion of the cyclophilin-60 protein which retains common epitopes with the full length protein.

In one embodiment, the antibodies or proteins may be directly or indirectly labelled. By "labelled" herein is meant a compound that has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position. Thus, for example, the cyclophilin-60 protein antibody may be labelled for detection, or a secondary antibody to the cyclophilin-60 protein antibody may be created and labelled.

In one embodiment, the antibodies generated to the cyclophilin-60 proteins of the invention are used to purify or separate cyclophilin-60 proteins from a sample. Thus, for example, antibodies generated to cyclophilin-60 proteins which will bind to the protein may be immobilized, using standard technology, for affinity chromatography to isolate the protein from tissue samples.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLES

Example 1

Identification and Cloning of Cyclophilin-60

The yeast two-hybrid system (Fields et al., Nature 340:245–246 (1989)) has been used to identify the interactions of a number of interesting proteins, including HIV Gag and cyclophilin A, TGF-beta receptor and FKBP-12, and Ras and Raf (Luban et al., Cell 73:1067–78 (1993); Wang et al., Science 265:674–676 (1994); and Vojtek et al., Cell 74:205–214 (1993)). This system is suitable for isolating proteins which are active as fusion proteins with the yeast GAL4 activation domain. For example, serine proteases require a free amino terminus for proper protein folding and therefore are not appropriate for use in the yeast system. Eglin c is a well characterized potent leech inhibitor of chymotrypsin, subtilisin and cathepsin G, and is a suitable candidate for use in the yeast system due to its small size and lack of disulfide bonds. A schematic of the yeast two hybrid system is shown in FIG. 1A.

An eglin c gene (Genbank accession number X00802) (SEQ ID NO:1) containing sequences encoding the M2 Flag epitope (DYKDDDDK, Eastman Kodak) (SEQ ID NO:2) at the 3' end was synthesized by PCR using overlapping oligonucleotides. The eglin fusion gene (SEQ ID NO:1) was cloned into the plasmid pGBT9 (pBDeglin) and used in the yeast two-hybrid system as described (Clontech). Briefly, S. cerevisiae strain HF7c (Clontech) was transformed sequentially with pBDeglin and a B lymphocyte cDNA library (Clontech) that contained GAL4 activation domain fusion genes. Colonies that contained plasmids encoding potentially interacting proteins were selected on the appropriate synthetic medium and assayed for beta-galactosidase activity to confirm the in vivo interaction (Clontech). About 130,000 clones of the B lymphocyte library were screened and three identical true positive clones (pAD16.1) were isolated.

To confirm that pAD16.1 was interacting specifically with eglin c (SEQ ID NO:1), we performed a series of control transformations with yeast strain HF7c (Figure 1B). When pAD16.1 or the DNA-binding domain/eglin M2 tag plasmid (pBDeglin) was each transformed alone, all the resulting colonies remained white when assayed for beta-galactosidase activity, indicating the absence of a specific interaction. Similarly, when pAD16.1 was cotransformed with a plasmid containing the DNA-binding domain/tumor suppression gene p53 fusion (pVA3), all the colonies remained white. Only when pAD16.1 was cotransformed with pBDeglin did all the colonies turn blue, indicating a specific interaction between the two proteins. Colonies that contained plasmids (pVA3 and pTD1) encoding proteins that are known to interact, the tumor suppressor gene p53 and SV40 large T antigen, also turned blue. In addition, the positive interaction between pBDeglin and pAD16.1 was verified in another yeast strain (SFY526) that contains a different promoter controlling the lacZ reporter gene than strain HF7c.

The pAD16.1 clone was used to probe $2\times10^6$ clones a Raji cDNA library (Clontech) and two additional cDNAs (clones 6.1 and 26.1) were isolated. Clone 6.1 encoded the entire protein and was used in all subsequent cloning and expression experiments. Clone 6.1 was sequenced in both directions using an Applied Biosystems Model sequencer, and the cDNA and the complete predicted amino acid sequence of the longest clone are shown in FIG. 2 (SEQ ID NO:4). All three cDNAs have overlapping identical coding sequences but different 3' untranslated regions (see FIG. 8) (SEQ ID NOS:20 and 21). The protein sequence has the characteristic "signature" amino acids (residues 289–307 and 316–334) that have been noted in the cyclophilin family. There are a number of potential protein kinase A, protein kinase C, and glycogen synthase kinase-3 phosphorylation sites throughout the protein and three triplets of lysine residues which may represent nuclear localization sequences. A potential polyA site was identified in the cDNA starting at 1757. No other structural motifs were detected other than the cyclophilin domain, although it is possible that two similar repeats, shown in FIG. 3C (SEQ ID NOS:4 and 19), represents a motif of unknown function. The predicted protein has a calculated pI of 9 and an expected molecular weight of 60 kD.

Example 2

Expression of cyclophilin-60 in tissue

The cyclophllin-60 cDNA (SEQ ID NO:3) was used to probe multiple tissue and cancer cell line Northern blots at high stringency (FIG. 4). A '3 and '4.4 kb transcript was detected in most normal tissues examined. The highest level of expression was seen in pancreas, thymus, and testis while low expression was seen in brain and peripheral blood leukocytes. The two transcripts appeared to be present in equal relative levels in all tissues with the exception of testis, small intestine and colon, where the 4.4. kb transcript was expressed at a higher level. The same two transcripts were observed in cancer cell lines with the K562 cell line expression the highest levels. Interestingly, both testis and K-562 cells had an additional 2 kb transcript. These various transcripts may represent mRNAs with different 3' untranslated regions since three cDNAs that had different 3' untranslated regions were isolated. Two of the clones, pAD16.1 and 26.1, are shown in FIG. 8 (SEQ ID NOS:20 and 21). The 3' untranslated region of clone 6.1 is shown in FIG. 2. Clone 6.1 had an in-frame stop codon 54 basepairs upstream of the first ATG. The first six nucleotides after the stop codon are identical in each clone, with the following nucleotides being different. The numbering shown in FIG. 8 (SEQ ID NOS:20 and 21) is based on the basepairs of each clone.

A cyclophilin-60 cDNA (clone 6.1) (SEQ ID NO:3) was cloned into the pet11c vector (Novagen). Cyclophilin-60 expression in E. coli strain BL21(DE3) was induced for two hours with 0.4 mM isopropyl-beta-D-thiogalactopyranoside. The insoluble '60 kD protein was excised from SDS-PAGE gels and electroeluted as described (Current Protocols in Molecular Biology, Ed. Ausubel et al., Greene Publishing Associates, Inc. John Wiley & Sons, Inc.). The electroeluted protein was used to immunize rabbits (EL Labs, Soquel, Calif.). The antiserum was affinity purified by incubation with nitrocellulose strips containing immobilized bacterially produced cyclophilin-60. The antibodies were eluted in 50 mM glycine, pH 2.5, neutralized with 1M Hepes, pH 7.4, incubated with an acetone extract of BL21(DE3), and desalted with a G25 NAP-10 column (Pharmacia).

The purified antibodies were used to probe a human multiple tissue western blot. An immunoreactive 68 kD band was detected at the highest level in kidney tissue and lower levels in brain, heart, and lung tissue (FIG. 5A). The 68 kD band was not detected in skeletal muscle and liver possible due to low expression levels even though the Northern blots show mRNA in these tissues. Several other bands ranging from 40 kD to 60 kD were also detected. These bands were specific to the cyclophilin-60 antiserum since they were not detected when the blot was probed only with the secondary antibody. A similar pattern of bands was seen when COS-7 cells were transiently transfected with an cyclophilin-60-Flag fusion gene (Figure 5B). The lower molecular weight proteins most likely represent processed forms of the full length precursor. There was a predominant 50 kD band, which most likely represents a loss of at least 100 amino acids from the N-terminus. This band may result from post-translational modification, such as a proteolytic cleavage, or optionally from alternatively spliced mRNA forms.

Example 3

Localization of Cyclophilin-60

To determine the subcellular location of cyclophilin-60, transient transfection of a cyclophilin-60-Flag fusion gene into COS-7 cells was done, with indirect immunofluorescence. The cyclophilin-60-Flag fusion gene was cloned into the expression vector pcDNA3 (Invitrogen). COS-7 cells were transfected by the DEAE-dextran method and expression of cyclophilin-60 in untransfected and transiently transfected cells was confirmed by western blotting with the M2 monoclonal antibody. For indirect immunofluorescence experiments, untransfected and transiently transfected COS-7 cells were stained with the M2 monoclonal antibody (30 ug/ml), rhodamine-labelled goat anti-mouse IgG (1 ug/ml), and Hoechst dye (10 ug/ml) as described previously (Fisher et al., Cell 54:813–822 (1988)). The K-562 cell line was stained in a similar manner using control rabbit IgG or affinity purified anti-cyclophilin-60 antiserum and fluorescein-labelled goat anti-rabbit IgG.

The vast majority of immunoreactivity was localized to the nucleus, as determined by containing the cells with Hoechst dye, a DNA binding stain (FIG. 6A–C). No immunoreactivity was detected in untransfected COS cells (data not shown). Confocal microscopy of the cells revealed immunoreactivity within the nucleus and not in the nuclear membrane (data not shown). To rule out the possibility that nuclear staining was an artifact of overexpression in COS-7 cells, indirect immunofluorescence on the K-562 cell line was also done, which is a human chronic myelogenous leukemic cell line, using polyclonal rabbit affinity purified anti-cyclophilin-60 antiserum (data not shown). Immunoreactivity that coincided with Hoechst staining was detected with the specific antiserum but not with control rabbit IgG, confirming the nuclear localization of cyclophilin-60 in transiently transfected COS cells.

Example 4

Immunohistochemical Localization of Cyclophilin-60 Various Human Tissues

Sections of human tissue were stained with affinity purified rabbit anti-cyclophilin-60 antiserum. The paraffin sections (BioGenex) were prepared as described previously (Cattoretti et al., J. of Pathology 168:357 (1992), visualized using the Stravigen detection system (BioGenex) and counterstained with Fast Green. The cyclophilin-60 antiserum was prepared as described in Example 2. No staining was seen on control slides with rabbit IgG. The results are shown in FIG. 7.

Example 5

Stable Expression of cyclophilin-60 in a mammalian cell line

COS-7 cells were electroporated essentially as described (Current Protocols in Molecular Biology, Ed. Ausubel et al., Greene Publishing Associates, Inc., John Wiley & Sons, INc.) with the pcDNA3 expression vector or the cyclophilin-60 Flag fusion gene (cloned in the pcDNA3 vector). Both DNAs were linearized with the AvrII restriction enzyme prior to electroporation. Three days post transfection, cells were transferred into complete medium containing 0.8 mg/ml Geneticin (Gibco BRL). Stable clones were isolated 14 days post transfection. Selected clones were expanded and analyzed by western blotting with the M2 monoclonal antibody. A 68 kD immunoreactive band was detected in three independent cyclophilin-60 transfected clones but not in pcDNA3-transfected control clones (data not shown).

We claim:

1. A recombinant cyclophilin-60 protein which interacts with an eglin c protein and has an amino acid sequence at least about 95% identical to that shown in FIG. 2 (SEQ ID NO:4).

2. A recombinant cyclophilin-60 protein which has the amino acid sequence shown in FIG. 2 (SEQ ID NO:4).

3. A recombinant cyclophilin-60 protein that interacts with eglin c protein and is encoded by a nucleic acid that will hybridize under high stringency conditions to the nucleic acid sequence shown in FIG. 2 (SEQ ID NO:3).

4. A recombinant cyclophilin-60 protein that interacts with an eglin c protein and is encoded by a nucleic acid comprising a DNA having a sequence at least about 90% identical to that shown in FIG. 2 (SEQ ID NO:3).

5. A recombinant nucleic acid encoding a cyclophilin-60 protein, nucleic acid comprising DNA having a sequence at least about 90% identical to that shown in FIG. 2 (SEQ ID NO:3).

6. A recombinant nucleic acid encoding a cyclophilin-60 protein, said nucleic acid comprising DNA that will hybridize under high stringency conditions to the nucleic acid sequence shown in FIG. 2 (SEQ ID NO:3).

7. A recombinant nucleic acid encoding a cyclophilin-60 protein, said nucleic acid comprising DNA that encodes the amino acid sequence shown in FIG. 2 (SEQ ID NO:4).

8. A recombinant nucleic acid encoding a cyclophilin-60 protein, said nucleic acid comprising DNA having the sequence shown in FIG. 2 (SEQ ID NO:3).

9. An expression vector comprising transcriptional and translational regulatory DNA operably linked to DNA encoding the recombinant cyclophilin-60 protein according to claims 1, 2, 3, or 4.

10. A host cell transformed with an expression vector according to claim 9.

11. A method of producing a cyclophilin-60 protein comprising:
    a) cults a host cell transformed with an expression vector comprising transcriptional and translational regulatory DNA operably linked to DNA encoding the recombinant cyclophilin-60 protein according to claim 1, 2, 3, or 4; and
    b) expressing said DNA to produce a cyclophilin-60 protein.

12. A host cell transformed with the nucleic acid of claim 5, 6, 7, or 8.

13. A recombinant nucleic acid encoding a cyclophilin 60 protein comprising an amino acid sequence at least about 95% identical to that shown in FIG. 2 (SEQ ID NO:4).

\* \* \* \* \*

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 6 amino acids
      (B) TYPE: amino acid
      (C) STRANDEDNESS: unknown
      (D) TOPOLOGY: unknown (ii) MOLECULE TYPE: protein (xi) SEQUENCE DESCRIPTION: SEQ ID NO:1:

Val Thr Leu Asp Leu Arg
1               5

(2) INFORMATION FOR SEQ ID NO:2:

(i) SEQUENCE CHARACTERISTICS:
      (A) LENGTH: 8 amino acids
      (B) TYPE: amino acid
      (C) STRANDEDNESS: unknown
      (D) TOPOLOGY: unknown (ii) MOLECULE TYPE: protein (xi) SEQUENCE DESCRIPTION: SEQ ID NO:2:

Asp Tyr Lys Asp Asp Asp Asp Lys
1               5

(2) INFORMATION FOR SEQ ID NO:3:

```
    (i) SEQUENCE CHARACTERISTICS:
        (A) LENGTH: 2589 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: CDS
        (B) LOCATION: 93..1652

(xi) SEQUENCE DESCRIPTION: SEQ ID NO:3:

CCCCCCCCCC CCCCGAACTC GGCTGCGGCT CCATGGTCTG AGTTGTCAGC CGTTGTTTTT           60

TCGTGCTCGC TAGTCGCCGC CGCCGCTCCG CC ATG GGG AAG CGA CAG CAC CAA           113
                                   Met Gly Lys Arg Gln His Gln
                                     1               5

AAG GAC AAA ATG TAC ATT ACC TGT GCT GAA TAC ACT CAC TTT TAT GGT           161
Lys Asp Lys Met Tyr Ile Thr Cys Ala Glu Tyr Thr His Phe Tyr Gly
         10                  15                  20

GGC AAG AAG CCA GAT CTC CCA CAA ACA AAT TTT CGT CGT TTA CCT TTT           209
Gly Lys Lys Pro Asp Leu Pro Gln Thr Asn Phe Arg Arg Leu Pro Phe
     25                  30                  35

GAC CAC TGC AGT CTC TCT CTG CAG CCC TTT GTC TAC CCA GTC TGC ACT           257
Asp His Cys Ser Leu Ser Leu Gln Pro Phe Val Tyr Pro Val Cys Thr
 40                  45                  50                  55

CCC GAT GGC ATC GTC TTT GAC TTA CTG AAC ATT GTT CCA TGG CTT AAG           305
Pro Asp Gly Ile Val Phe Asp Leu Leu Asn Ile Val Pro Trp Leu Lys
                 60                  65                  70

AAG TAC GGG ACC AAC CCC AGC AAT GGA GAG AAG CTG GAC GGG AGG TCC           353
Lys Tyr Gly Thr Asn Pro Ser Asn Gly Glu Lys Leu Asp Gly Arg Ser
             75                  80                  85

CTG ATC AAG CTG AAC TTT TCC AAG AAC AGT GAG GGG AAG TAC CAC TGC           401
Leu Ile Lys Leu Asn Phe Ser Lys Asn Ser Glu Gly Lys Tyr His Cys
         90                  95                 100

CCA GTG CTG TTT ACC GTG TTC ACC AAC AAC ACC CAC ATC GTG GCT GTG           449
Pro Val Leu Phe Thr Val Phe Thr Asn Asn Thr His Ile Val Ala Val
     105                 110                 115

AGG ACG ACC GGC AAC GTC TAC GCC TAT GAG GCA GTG GAA CAG CTA AAT           497
Arg Thr Thr Gly Asn Val Tyr Ala Tyr Glu Ala Val Glu Gln Leu Asn
120                 125                 130                 135

ATC AAG GCC AAG AAC TTC CGG GAC CTG CTG ACC GAC GAG CCC TTC TCC           545
Ile Lys Ala Lys Asn Phe Arg Asp Leu Leu Thr Asp Glu Pro Phe Ser
                140                 145                 150

CGG CAG GAC ATC ATC ACC CTC CAG GAC CCC ACC AAT TTG GAC AAG TTC           593
Arg Gln Asp Ile Ile Thr Leu Gln Asp Pro Thr Asn Leu Asp Lys Phe
            155                 160                 165

AAT GTC TCT AAC TTC TAT CAT GTG AAG AAT AAC ATG AAA ATA ATA GAC           641
Asn Val Ser Asn Phe Tyr His Val Lys Asn Asn Met Lys Ile Ile Asp
        170                 175                 180

CCA GAT GAA GAG AAG GCC AAA CAG GAC CCG TCT TAT TAT CTG AAA AAT           689
Pro Asp Glu Glu Lys Ala Lys Gln Asp Pro Ser Tyr Tyr Leu Lys Asn
185                 190                 195

ACA AAT GCC GAG ACC CGA GAG ACC CTG CAG GAG CTC TAC AAG GAG TTC           737
Thr Asn Ala Glu Thr Arg Glu Thr Leu Gln Glu Leu Tyr Lys Glu Phe
200                 205                 210                 215

AAA GGG GAC GAG ATT CTG GCA GCC ACC ATG AAG GCC CCG GAG AAG AAG           785
Lys Gly Asp Glu Ile Leu Ala Ala Thr Met Lys Ala Pro Glu Lys Lys
                220                 225                 230

AAA GTG GAC AAG CTG AAT GCT GCC CAC TAT TCC ACA GGG AAG GTC AGC           833
Lys Val Asp Lys Leu Asn Ala Ala His Tyr Ser Thr Gly Lys Val Ser
            235                 240                 245
```

-continued

| | | |
|---|---|---|
| GCT TCC TTC ACC TCC ACC GCG ATG GTC CCG GAG ACC ACA CAT GAA GCA<br>Ala Ser Phe Thr Ser Thr Ala Met Val Pro Glu Thr Thr His Glu Ala<br>          250                   255                 260 | 881 |
| GCT GCC ATC GAC GAG GAT GTG CTG CGC TAC CAG TTT GTG AAG AAG AAG<br>Ala Ala Ile Asp Glu Asp Val Leu Arg Tyr Gln Phe Val Lys Lys Lys<br>265                   270                   275 | 929 |
| GGC TAC GTG CGG CTG CAC ACC AAC AAG GGC GAC CTC AAC CTG GAG CTG<br>Gly Tyr Val Arg Leu His Thr Asn Lys Gly Asp Leu Asn Leu Glu Leu<br>280                   285                   290                 295 | 977 |
| CAC TGC GAC CTG ACA CCA AAA ACC TGC GAA AAC TTC ATC AGG CTT TGC<br>His Cys Asp Leu Thr Pro Lys Thr Cys Glu Asn Phe Ile Arg Leu Cys<br>                  300                   305               310 | 1025 |
| AAG AAG CAT TAT TAC GAT GGC ACC ATC TTC CAC AGA TCC ATC CGG AAC<br>Lys Lys His Tyr Tyr Asp Gly Thr Ile Phe His Arg Ser Ile Arg Asn<br>          315                   320                   325 | 1073 |
| TTT GTG ATC CAA GGG GGC GAC CCC ACA GGC ACA GGC ACG GGT GGG GAG<br>Phe Val Ile Gln Gly Gly Asp Pro Thr Gly Thr Gly Thr Gly Gly Glu<br>330                   335                   340 | 1121 |
| TCA TAC TGG GGG AAG CCC TTC AAA GAC GAG TTC CGG CCC AAC CTC TCG<br>Ser Tyr Trp Gly Lys Pro Phe Lys Asp Glu Phe Arg Pro Asn Leu Ser<br>          345                   350                   355 | 1169 |
| CAC ACG GGC CGC GGC ATC CTC AGC ATG GCC AAC TCC GGG CCC AAC AGC<br>His Thr Gly Arg Gly Ile Leu Ser Met Ala Asn Ser Gly Pro Asn Ser<br>360                   365                   370                 375 | 1217 |
| AAC AGG TCT CAA TTC TTC ATC ACG TTT CGC TCC TGT GCC TAC CTG GAC<br>Asn Arg Ser Gln Phe Phe Ile Thr Phe Arg Ser Cys Ala Tyr Leu Asp<br>                  380                   385               390 | 1265 |
| AAG AAG CAT ACC ATC TTT GGA CGG GTT GTT GGG GGC TTT GAC GTA CTG<br>Lys Lys His Thr Ile Phe Gly Arg Val Val Gly Gly Phe Asp Val Leu<br>          395                   400                   405 | 1313 |
| ACA GCC ATG GAG AAT GTG GAG AGT GAC CCC AAA ACT GAC CGC CCT AAG<br>Thr Ala Met Glu Asn Val Glu Ser Asp Pro Lys Thr Asp Arg Pro Lys<br>410                   415                   420 | 1361 |
| GAG GAG ATC CGC ATT GAT GCC ACT ACA GTG TTC GTG GAC CCC TAT GAG<br>Glu Glu Ile Arg Ile Asp Ala Thr Thr Val Phe Val Asp Pro Tyr Glu<br>          425                   430                   435 | 1409 |
| GAG GCC GAT GCC CAG ATT GCG CAG GAG CGG AAG ACA CAG CTC AAG GTA<br>Glu Ala Asp Ala Gln Ile Ala Gln Glu Arg Lys Thr Gln Leu Lys Val<br>440                   445                   450                 455 | 1457 |
| GCC CCG GAG ACC AAA GTG AAG AGC AGC CAG CCC CAG GCA GGG AGC CAG<br>Ala Pro Glu Thr Lys Val Lys Ser Ser Gln Pro Gln Ala Gly Ser Gln<br>                  460                   465               470 | 1505 |
| GGC CCC CAG ACC TTC CGC CAG GGC GTG GGC AAG TAC ATC AAC CCA GCA<br>Gly Pro Gln Thr Phe Arg Gln Gly Val Gly Lys Tyr Ile Asn Pro Ala<br>          475                   480                   485 | 1553 |
| GCC ACG AAG CGA GCA GCA GAG GAA GAG CCC TCA ACC AGT GCC ACT GTC<br>Ala Thr Lys Arg Ala Ala Glu Glu Glu Pro Ser Thr Ser Ala Thr Val<br>490                   495                   500 | 1601 |
| CCC ATG TCC AAG AAG AAG CCC AGT CGG GGT TTT GGG GAC TTC AGC TCC<br>Pro Met Ser Lys Lys Lys Pro Ser Arg Gly Phe Gly Asp Phe Ser Ser<br>505                   510                   515 | 1649 |
| TGG TAGCAGCAGG TTGGCCGCTG TGGACCTTGG TGGGGTTGCA GGGCTGGGGG<br>Trp<br>520 | 1702 |

CCCATGTCCA CATCTCCATT TCCAGCCTTT CTAGCCTGCC CTCTGCTGCC AGCCAATAAA 1762

TTGCTTGCCT GCTGCCTGCA TCCCCTTTCC TGGCCCCTGG GAGCCCACAG CCTTCCCATC 1822

CCTTAACCTG TTGCCAAGGG CCTTGGCCCT GTTTCCAGGA CCTGGCCCAG CCAGAGCCCA 1882

CTGCTGGGAC CTTCAAGCAC AAGGCCTGCC CTACACCCAG GCTGGTGCCT CAGGCCTCTC 1942

-continued

```
CTCTAGTAGG CAGGCCAGGT TAGTGAGGAA GGACTGTGTC TCCAGATTGT GGTTTCCTCT    2002

TTAAGACAGG GTCTTGCTCT GTTACCCAGG CTCCAGTGCA GTGGTGTGAT CATGGCTCAC    2062

TGCAGCCTCG ACCTCCTGGG CTCAAGCAAT CCTCCTGCCT CAGCCTCGCA AGTAGCTGGG    2122

ACTACAGCCG TGCACCACTA CATCCAGCTG TATATGTCTG GTTTTCTTAC CCCTACTTCT    2182

GTCATCTTCT CAGGGACAGC CTATTTATAC AACCAGTGTG GTCCCCTGAC CAACGCCATT    2242

ACCTGGGACA AGTTTTCAGA CCCCAGACTT ACTGAGCCTA AGCCTCTGCA GGGTGGGCTT    2302

CTCGGTCTGT TTTGACAAAA CTTCAGGGGC TTCTGAAGGC TGGTGTTGGA CGGCAGCATT    2362

GAGTTTCCTG CCGTGCCCTG CCTGAGCTCT CAGGGCCCTG CTCACCTGCT CTGGCTGTGA    2422

ACCACCTGGG CTTCATCTCA AGCCTGCCTG GCGTCTCTGT GCCCCTGTGA GAATCTTGAG    2482

GGGACCCACA CTGGGTTGAG GCCAGTGTCT CCTGCTGTGA GAACAAGTGG ATGTCCCTCT    2542

CCCCGCCCTC CTGCTGAAGT GGCCTTGCTG CTCTCAGGCC CGGCCAG                  2589
```

(2) INFORMATION FOR SEQ ID NO:4:

(i) SEQUENCE CHARACTERISTICS:
        (A) LENGTH: 520 amino acids
        (B) TYPE: amino acid
        (D) TOPOLOGY: linear (ii) MOLECULE TYPE: protein (xi) SEQUENCE DESCRIPTION: SEQ ID NO:4:

```
Met Gly Lys Arg Gln His Gln Lys Asp Lys Met Tyr Ile Thr Cys Ala
 1               5                  10                  15

Glu Tyr Thr His Phe Tyr Gly Gly Lys Lys Pro Asp Leu Pro Gln Thr
                20                  25                  30

Asn Phe Arg Arg Leu Pro Phe Asp His Cys Ser Leu Ser Leu Gln Pro
            35                  40                  45

Phe Val Tyr Pro Val Cys Thr Pro Asp Gly Ile Val Phe Asp Leu Leu
        50                  55                  60

Asn Ile Val Pro Trp Leu Lys Lys Tyr Gly Thr Asn Pro Ser Asn Gly
 65                  70                  75                  80

Glu Lys Leu Asp Gly Arg Ser Leu Ile Lys Leu Asn Phe Ser Lys Asn
                85                  90                  95

Ser Glu Gly Lys Tyr His Cys Pro Val Leu Phe Thr Val Phe Thr Asn
            100                 105                 110

Asn Thr His Ile Val Ala Val Arg Thr Thr Gly Asn Val Tyr Ala Tyr
        115                 120                 125

Glu Ala Val Glu Gln Leu Asn Ile Lys Ala Lys Asn Phe Arg Asp Leu
    130                 135                 140

Leu Thr Asp Glu Pro Phe Ser Arg Gln Asp Ile Ile Thr Leu Gln Asp
145                 150                 155                 160

Pro Thr Asn Leu Asp Lys Phe Asn Val Ser Asn Phe Tyr His Val Lys
                165                 170                 175

Asn Asn Met Lys Ile Ile Asp Pro Asp Glu Lys Ala Lys Gln Asp
            180                 185                 190

Pro Ser Tyr Tyr Leu Lys Asn Thr Asn Ala Glu Thr Arg Glu Thr Leu
        195                 200                 205

Gln Glu Leu Tyr Lys Glu Phe Lys Gly Asp Glu Ile Leu Ala Ala Thr
    210                 215                 220

Met Lys Ala Pro Glu Lys Lys Val Asp Lys Leu Asn Ala Ala His
225                 230                 235                 240

Tyr Ser Thr Gly Lys Val Ser Ala Ser Phe Thr Ser Thr Ala Met Val
```

```
                        245                 250                 255
Pro Glu Thr Thr His Glu Ala Ala Ile Asp Glu Asp Val Leu Arg
            260                 265                 270

Tyr Gln Phe Val Lys Lys Gly Tyr Val Arg Leu His Thr Asn Lys
        275                 280                 285

Gly Asp Leu Asn Leu Glu Leu His Cys Asp Leu Thr Pro Lys Thr Cys
    290                 295                 300

Glu Asn Phe Ile Arg Leu Cys Lys Lys His Tyr Tyr Asp Gly Thr Ile
305                 310                 315                 320

Phe His Arg Ser Ile Arg Asn Phe Val Ile Gln Gly Gly Asp Pro Thr
                325                 330                 335

Gly Thr Gly Thr Gly Gly Glu Ser Tyr Trp Gly Lys Pro Phe Lys Asp
            340                 345                 350

Glu Phe Arg Pro Asn Leu Ser His Thr Gly Arg Gly Ile Leu Ser Met
        355                 360                 365

Ala Asn Ser Gly Pro Asn Ser Asn Arg Ser Gln Phe Phe Ile Thr Phe
    370                 375                 380

Arg Ser Cys Ala Tyr Leu Asp Lys Lys His Thr Ile Phe Gly Arg Val
385                 390                 395                 400

Val Gly Gly Phe Asp Val Leu Thr Ala Met Glu Asn Val Glu Ser Asp
                405                 410                 415

Pro Lys Thr Asp Arg Pro Lys Glu Glu Ile Arg Ile Asp Ala Thr Thr
            420                 425                 430

Val Phe Val Asp Pro Tyr Glu Glu Ala Asp Ala Gln Ile Ala Gln Glu
        435                 440                 445

Arg Lys Thr Gln Leu Lys Val Ala Pro Glu Thr Lys Val Lys Ser Ser
450                 455                 460

Gln Pro Gln Ala Gly Ser Gln Gly Pro Gln Thr Phe Arg Gln Gly Val
465                 470                 475                 480

Gly Lys Tyr Ile Asn Pro Ala Ala Thr Lys Arg Ala Ala Glu Glu Glu
                485                 490                 495

Pro Ser Thr Ser Ala Thr Val Pro Met Ser Lys Lys Lys Pro Ser Arg
            500                 505                 510

Gly Phe Gly Asp Phe Ser Ser Trp
        515                 520

(2) INFORMATION FOR SEQ ID NO:5:

(i) SEQUENCE CHARACTERISTICS:
        (A) LENGTH: 123 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:5:

Gly Asp Leu Asn Leu Glu Leu His Cys Asp Leu Thr Pro Lys Thr Cys
1               5                   10                  15

Glu Asn Phe Ile Arg Leu Cys Lys Lys His Tyr Tyr Asp Gly Thr Ile
            20                  25                  30

Phe His Arg Ser Ile Arg Asn Phe Val Ile Gln Gly Gly Asp Pro Thr
        35                  40                  45

Gly Thr Gly Thr Gly Gly Glu Ser Tyr Trp Gly Lys Pro Phe Lys Asp
    50                  55                  60

Glu Phe Arg Pro Asn Leu Ser His Thr Gly Arg Gly Ile Leu Ser Met
65                  70                  75                  80
```

```
Ala Asn Ser Gly Pro Asn Ser Asn Arg Ser Gln Phe Phe Ile Thr Phe
                 85                  90                  95

Arg Ser Cys Ala Tyr Leu Asp Lys Lys His Thr Ile Phe Gly Arg Val
            100                 105                 110

Val Gly Gly Phe Asp Val Leu Thr Ala Met Glu
        115                 120
```

(2) INFORMATION FOR SEQ ID NO:6:

(i) SEQUENCE CHARACTERISTICS:
        (A) LENGTH: 123 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:6:

```
Gly Pro Leu Asn Leu Glu Leu Phe Ala Pro Lys Val Pro Lys Ala Cys
1               5                  10                  15

Glu Asn Phe Ile Thr His Cys Ser Asn Gly Tyr Tyr Asn Asn Thr Lys
                20                  25                  30

Phe His Arg Leu Ile Lys Asn Phe Met Leu Gln Gly Gly Asp Pro Thr
            35                  40                  45

Gly Thr Gly His Gly Gly Glu Ser Ile Trp Asp Lys Pro Phe Ser Asp
    50                  55                  60

Glu Phe Ile Ser Gly Phe Ser His Asp Ala Arg Gly Val Leu Ser Met
65              70                  75                  80

Ala Asn Lys Gly Ser Asn Thr Asn Gly Ser Gln Phe Phe Ile Thr Phe
                85                  90                  95

Arg Pro Cys Lys Tyr Leu Asp Arg Lys His Thr Ile Phe Gly Arg Leu
            100                 105                 110

Val Gly Gly Gln Asp Thr Leu Thr Thr Ile Glu
        115                 120
```

(2) INFORMATION FOR SEQ ID NO:7:

(i) SEQUENCE CHARACTERISTICS:
        (A) LENGTH: 123 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:7:

```
Gly Asp Ile Lys Ile Glu Leu Tyr Val Asp Asp Ala Pro Lys Ala Cys
1               5                  10                  15

Glu Asn Phe Leu Ala Leu Cys Ala Ser Asp Tyr Tyr Asn Gly Cys Ile
                20                  25                  30

Phe His Arg Asn Ile Lys Asp Phe Met Val Gln Thr Gly Asp Pro Thr
            35                  40                  45

His Ser Gly Lys Gly Gly Glu Ser Ile Trp Gly Gly Pro Phe Glu Asp
    50                  55                  60

Glu Phe Val Ser Ala Leu Lys His Asp Ser Arg Gly Cys Val Ser Met
65              70                  75                  80

Ala Asn Asn Gly Pro Asp Ser Asn Arg Ser Gln Phe Phe Ile Thr Tyr
                85                  90                  95

Ala Lys Gln Ala His Leu Asp Met Lys Tyr Thr Leu Phe Gly Lys Val
            100                 105                 110
```

```
Ile Asp Gly Phe Asp Thr Leu Glu Glu Ile Glu
        115                 120
```

(2) INFORMATION FOR SEQ ID NO:8:

(i) SEQUENCE CHARACTERISTICS:
        (A) LENGTH: 123 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:8:

```
Gly Asp Ile His Thr Lys Leu Phe Pro Val Glu Cys Pro Lys Thr Val
1               5                   10                  15

Glu Asn Phe Cys Val His Ser Arg Asn Gly Tyr Tyr Asn Gly His Thr
            20                  25                  30

Phe His Arg Ile Ile Lys Gly Phe Met Ile Gln Thr Gly Asp Pro Thr
        35                  40                  45

Gly Thr Gly Met Gly Gly Glu Ser Ile Trp Gly Glu Phe Glu Asp
50                  55                  60

Glu Phe His Ser Thr Leu Arg His Asp Arg Pro Tyr Thr Leu Ser Met
65                  70                  75                  80

Ala Asn Ala Gly Ser Asn Thr Asn Gly Ser Gln Phe Phe Ile Thr Val
                85                  90                  95

Val Pro Thr Pro Trp Leu Asp Asn Lys His Thr Val Phe Gly Arg Val
                100                 105                 110

Thr Lys Gly Met Glu Val Val Gln Arg Ile Ser
        115                 120
```

(2) INFORMATION FOR SEQ ID NO:9:

(i) SEQUENCE CHARACTERISTICS:
        (A) LENGTH: 127 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:9:

```
Gly Arg Val Ser Phe Glu Leu Phe Ala Asp Lys Val Pro Lys Thr Ala
1               5                   10                  15

Glu Asn Phe Arg Ala Leu Ser Thr Gly Glu Lys Gly Phe Gly Tyr Lys
            20                  25                  30

Gly Ser Cys Phe His Arg Ile Ile Pro Gly Phe Met Cys Gln Gly Gly
        35                  40                  45

Asp Phe Thr Arg His Asn Gly Thr Gly Gly Lys Ser Ile Tyr Gly Glu
50                  55                  60

Lys Phe Glu Asp Glu Asn Phe Ile Leu Lys His Thr Gly Pro Gly Ile
65                  70                  75                  80

Leu Ser Met Ala Asn Ala Gly Pro Asn Thr Asn Gly Ser Gln Phe Phe
                85                  90                  95

Ile Cys Thr Ala Lys Thr Glu Trp Leu Asp Gly Lys His Val Val Phe
                100                 105                 110

Gly Lys Val Lys Glu Gly Met Ile Asn Ile Val Glu Ala Met Glu
        115                 120                 125
```

(2) INFORMATION FOR SEQ ID NO:10:

(i) SEQUENCE CHARACTERISTICS:
    (A) LENGTH: 126 amino acids
    (B) TYPE: amino acid
    (C) STRANDEDNESS: unknown
    (D) TOPOLOGY: unknown (ii) MOLECULE TYPE: protein (xi) SEQUENCE DESCRIPTION: SEQ ID NO:10:

```
Gly Arg Val Ile Phe Gly Leu Phe Gly Lys Thr Val Pro Lys Thr Val
1               5                  10                  15

Asp Asn Phe Val Ala Leu Ala Thr Gly Glu Lys Gly Phe Gly Tyr Lys
                20                  25                  30

Asn Ser Lys Phe His Arg Val Ile Lys Asp Phe Met Ile Gln Gly Gly
            35                  40                  45

Asp Phe Thr Arg Gly Asp Gly Thr Gly Lys Ser Ile Tyr Gly Glu
    50                  55                  60

Arg Phe Pro Asp Glu Asn Phe Lys Leu Lys His Tyr Gly Pro Gly Trp
65                  70                  75                  80

Val Ser Met Ala Asn Ala Gly Lys Asp Thr Asn Gly Ser Gln Phe Phe
                85                  90                  95

Ile Thr Thr Val Lys Thr Ala Trp Leu Asp Gly Lys His Val Val Phe
                100                 105                 110

Gly Lys Val Leu Glu Gly Met Glu Val Val Arg Lys Val Glu
                115                 120                 125
```

(2) INFORMATION FOR SEQ ID NO:11:

(i) SEQUENCE CHARACTERISTICS:
       (A) LENGTH: 126 amino acids
       (B) TYPE: amino acid
       (C) STRANDEDNESS: unknown
       (D) TOPOLOGY: unknown (ii) MOLECULE TYPE: protein (xi) SEQUENCE DESCRIPTION: SEQ ID NO:11:

```
Gly Arg Ile Val Ile Gly Leu Phe Gly Lys Val Val Pro Lys Thr Val
1               5                  10                  15

Glu Asn Phe Val Ala Leu Ala Thr Gly Glu Lys Gly Tyr Gly Tyr Lys
                20                  25                  30

Gly Ser Lys Phe His Arg Val Ile Lys Asp Phe Met Ile Gln Gly Gly
            35                  40                  45

Asp Ile Thr Thr Gly Asp Gly Thr Gly Val Ser Ile Tyr Gly Glu
    50                  55                  60

Thr Phe Pro Asp Glu Asn Phe Lys Leu Lys His Tyr Gly Ile Gly Trp
65                  70                  75                  80

Val Ser Met Ala Asn Ala Gly Pro Asp Thr Asn Gly Ser Gln Phe Phe
                85                  90                  95

Ile Thr Leu Thr Lys Pro Thr Trp Leu Asp Gly Lys His Val Val Phe
                100                 105                 110

Gly Lys Val Ile Asp Gly Met Thr Val Val His Ser Ile Glu
                115                 120                 125
```

(2) INFORMATION FOR SEQ ID NO:12:

(i) SEQUENCE CHARACTERISTICS:
       (A) LENGTH: 126 amino acids
       (B) TYPE: amino acid
       (C) STRANDEDNESS: unknown
       (D) TOPOLOGY: unknown (ii) MOLECULE TYPE: protein (xi) SEQUENCE DESCRIPTION: SEQ ID NO:12:

| Gly | Arg | Val | Val | Leu | Glu | Leu | Lys | Ala | Asp | Val | Val | Pro | Lys | Thr | Ala |
|---|---|---|---|---|---|---|---|---|---|---|---|---|---|---|---|
| 1 | | | | 5 | | | | | 10 | | | | | 15 | |

| Glu | Asn | Phe | Arg | Ala | Leu | Cys | Thr | Gly | Glu | Lys | Gly | Phe | Gly | Tyr | Lys |
|---|---|---|---|---|---|---|---|---|---|---|---|---|---|---|---|
| | | | 20 | | | | | 25 | | | | | 30 | | |

| Gly | Ser | Thr | Phe | His | Arg | Val | Ile | Pro | Ser | Phe | Met | Cys | Gln | Ala | Gly |
|---|---|---|---|---|---|---|---|---|---|---|---|---|---|---|---|
| | | 35 | | | | | 40 | | | | | 45 | | | |

| Asp | Phe | Thr | Asn | His | Asn | Gly | Thr | Gly | Lys | Ser | Ile | Tyr | Gly | Ser |
|---|---|---|---|---|---|---|---|---|---|---|---|---|---|---|
| 50 | | | | | 55 | | | | | 60 | | | | |

| Arg | Phe | Pro | Asp | Glu | Asn | Phe | Thr | Leu | Lys | His | Val | Gly | Pro | Gly | Val |
|---|---|---|---|---|---|---|---|---|---|---|---|---|---|---|---|
| 65 | | | | | 70 | | | | | 75 | | | | | 80 |

| Leu | Ser | Met | Ala | Asn | Ala | Gly | Pro | Asn | Thr | Asn | Gly | Ser | Gln | Phe | Phe |
|---|---|---|---|---|---|---|---|---|---|---|---|---|---|---|---|
| | | | | 85 | | | | | 90 | | | | | 95 | |

| Ile | Cys | Thr | Ile | Lys | Thr | Asp | Trp | Leu | Asp | Gly | Lys | His | Val | Val | Phe |
|---|---|---|---|---|---|---|---|---|---|---|---|---|---|---|---|
| | | | 100 | | | | | 105 | | | | | 110 | | |

| Gly | His | Val | Lys | Glu | Gly | Met | Asp | Val | Val | Lys | Lys | Ile | Glu |
|---|---|---|---|---|---|---|---|---|---|---|---|---|---|
| | | 115 | | | | | 120 | | | | | 125 | |

(2) INFORMATION FOR SEQ ID NO:13:

(i) SEQUENCE CHARACTERISTICS:
        (A) LENGTH: 134 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:13:

| Gly | Arg | Ile | Val | Leu | Glu | Leu | Phe | Ala | Asp | Ile | Val | Pro | Lys | Thr | Ala |
|---|---|---|---|---|---|---|---|---|---|---|---|---|---|---|---|
| 1 | | | | 5 | | | | | 10 | | | | | 15 | |

| Glu | Asn | Phe | Arg | Ala | Leu | Cys | Thr | Gly | Glu | Lys | Gly | Ile | Gly | His | Thr |
|---|---|---|---|---|---|---|---|---|---|---|---|---|---|---|---|
| | | | 20 | | | | | 25 | | | | | 30 | | |

| Thr | Gly | Lys | Pro | Leu | His | Phe | Lys | Gly | Cys | Pro | Phe | His | Arg | Ile | Ile |
|---|---|---|---|---|---|---|---|---|---|---|---|---|---|---|---|
| | | 35 | | | | | 40 | | | | | 45 | | | |

| Lys | Lys | Phe | Met | Ile | Gln | Gly | Gly | Asp | Phe | Ser | Asn | Gln | Asn | Gly | Thr |
|---|---|---|---|---|---|---|---|---|---|---|---|---|---|---|---|
| 50 | | | | | 55 | | | | | 60 | | | | | |

| Gly | Gly | Glu | Ser | Ile | Tyr | Gly | Glu | Lys | Phe | Glu | Asp | Glu | Asn | Phe | His |
|---|---|---|---|---|---|---|---|---|---|---|---|---|---|---|---|
| 65 | | | | | 70 | | | | | 75 | | | | | 80 |

| Tyr | Lys | His | Asp | Arg | Glu | Gly | Leu | Leu | Ser | Met | Ala | Asn | Ala | Gly | Arg |
|---|---|---|---|---|---|---|---|---|---|---|---|---|---|---|---|
| | | | | 85 | | | | | 90 | | | | | 95 | |

| Asn | Thr | Asn | Gly | Ser | Gln | Phe | Phe | Ile | Thr | Thr | Val | Pro | Thr | Pro | His |
|---|---|---|---|---|---|---|---|---|---|---|---|---|---|---|---|
| | | | 100 | | | | | 105 | | | | | 110 | | |

| Leu | Asp | Gly | Lys | His | Val | Val | Phe | Gly | Gln | Val | Ile | Lys | Gly | Ile | Gly |
|---|---|---|---|---|---|---|---|---|---|---|---|---|---|---|---|
| | | | 115 | | | | | 120 | | | | | 125 | | |

| Val | Ala | Arg | Ile | Leu | Glu |
|---|---|---|---|---|---|
| 130 | | | | | |

(2) INFORMATION FOR SEQ ID NO:14:

(i) SEQUENCE CHARACTERISTICS:
        (A) LENGTH: 134 amino acids
        (B) TYPE: amino acid
        (C) STRANDEDNESS: unknown
        (D) TOPOLOGY: unknown (ii) MOLECULE TYPE: protein -continued (xi) SEQUENCE DESCRIPTION: SEQ ID NO:14:

Gly Arg Ile Met Phe Gln Leu Phe Ser Asp Ile Cys Pro Lys Thr Cys
1               5                   10                  15

Lys Asn Phe Leu Cys Leu Cys Ser Gly Glu Lys Gly Leu Gly Lys Thr
            20                  25                  30

Thr Gly Lys Lys Leu Cys Tyr Lys Gly Ser Thr Phe His Arg Val Val
        35                  40                  45

Lys Asn Phe Met Ile Gln Gly Asp Phe Ser Glu Gly Asn Gly Lys
        50                  55                  60

Gly Gly Glu Ser Ile Tyr Gly Gly Tyr Phe Lys Asp Glu Asn Phe Ile
65                  70                  75                  80

Leu Lys His Asp Arg Ala Phe Leu Leu Ser Met Ala Asn Arg Gly Lys
                85                  90                  95

His Thr Asn Gly Ser Gln Phe Phe Ile Thr Thr Lys Pro Ala Pro His
            100                 105                 110

Leu Asp Gly Val His Val Val Phe Gly Leu Val Ile Ser Gly Phe Glu
            115                 120                 125

Val Ile Glu Gln Ile Glu
        130

(2) INFORMATION FOR SEQ ID NO:15:

(i) SEQUENCE CHARACTERISTICS:
        (A) LENGTH: 126 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:15:

Gly Arg Ile Val Met Glu Leu Arg Ser Asp Val Val Pro Lys Thr Ala
1               5                   10                  15

Glu Asn Phe Arg Ala Leu Cys Thr Gly Glu Lys Gly Phe Gly Tyr Lys
            20                  25                  30

Gly Ser Ile Phe His Arg Val Ile Pro Asn Phe Met Cys Gln Gly Gly
        35                  40                  45

Asp Phe Thr Asn His Asn Gly Thr Gly Gly Lys Ser Ile Tyr Gly Asn
        50                  55                  60

Lys Phe Pro Asp Glu Asn Phe Glu Leu Lys His Thr Gly Ser Gly Ile
65                  70                  75                  80

Leu Ser Met Ala Asn Ala Gly Ala Asn Thr Asn Gly Ser Gln Phe Phe
                85                  90                  95

Ile Cys Thr Val Lys Thr Ala Trp Leu Asp Asn Lys His Val Val Phe
            100                 105                 110

Gly Glu Val Val Glu Gly Leu Asp Val Val Lys Lys Ile Glu
            115                 120                 125

(2) INFORMATION FOR SEQ ID NO:16:

(i) SEQUENCE CHARACTERISTICS:
        (A) LENGTH: 126 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:16:

Gly Arg Val Val Phe Lys Leu Tyr Asn Asp Ile Val Pro Lys Thr Ala

-continued

```
    1               5                   10                  15
Glu Asn Phe Arg Ala Leu Cys Thr Gly Glu Lys Gly Phe Gly Tyr Ala
                20                  25                  30
Gly Ser Pro Phe His Arg Val Ile Pro Asp Phe Met Leu Gln Gly Gly
                35                  40                  45
Asp Phe Thr Ala Gly Asn Gly Thr Gly Lys Ser Ile Tyr Gly Gly
        50                  55                  60
Lys Phe Pro Asp Glu Asn Phe Lys Lys His His Asp Arg Pro Gly Leu
65                  70                  75                  80
Leu Ser Met Ala Asn Ala Gly Pro Asn Thr Asn Gly Ser Gln Phe Phe
                85                  90                  95
Ile Thr Thr Val Pro Cys Pro Trp Leu Asp Gly Lys His Val Val Phe
                100                 105                 110
Gly Glu Val Val Asp Gly Tyr Asp Ile Val Lys Lys Val Glu
                115                 120                 125
```

(2) INFORMATION FOR SEQ ID NO:17:

(i) SEQUENCE CHARACTERISTICS:
        (A) LENGTH: 19 amino acids
        (B) TYPE: amino acid
        (C) STRANDEDNESS: unknown
        (D) TOPOLOGY: unknown (ii) MOLECULE TYPE: protein (ix) FEATURE:
        (A) NAME/KEY: Modified-site
        (B) LOCATION: 1
        (D) OTHER INFORMATION: /note= "The Xaa at position 1 can
            either be Glycine or Alanine."

(ix) FEATURE:
        (A) NAME/KEY: Modified-site
        (B) LOCATION: 3
        (D) OTHER INFORMATION: /note= "The Xaa at position 3 can
            any one of the following: Leucine, Isoleucine or Valine."

(ix) FEATURE:
        (A) NAME/KEY: Modified-site
        (B) LOCATION: 5
        (D) OTHER INFORMATION: /note= "The Xaa at position 5 can be
            any one of the following: Isoleucine, Valine, Methionine
            or Phenylalanine."

(ix) FEATURE:
        (A) NAME/KEY: Modified-site
        (B) LOCATION: 7
        (D) OTHER INFORMATION: /note= "The Xaa at position 7 can
            either be Leucine or Threonine."

(ix) FEATURE:
        (A) NAME/KEY: Modified-site
        (B) LOCATION: 14
        (D) OTHER INFORMATION: /note= "The Xaa at position 14 can
            be any one of the following: Lysine, Glutamic acid or
            Valine."

(ix) FEATURE:
        (A) NAME/KEY: Modified-site
        (B) LOCATION: 15
        (D) OTHER INFORMATION: /note= "The Xaa at position 14 can
            either be Threonine or Serine."

(ix) FEATURE:
        (A) NAME/KEY: Modified-site
        (B) LOCATION: 16
        (D) OTHER INFORMATION: /note= "The Xaa at position 16 can
            either be Alanine or Valine."

(xi) SEQUENCE DESCRIPTION: SEQ ID NO:17:

```
Xaa Xaa Xaa Xaa Xaa Xaa Xaa Xaa Xaa Xaa Xaa Xaa Pro Xaa Xaa Xaa
1               5                   10                  15

Xaa Asn Phe
```

(2) INFORMATION FOR SEQ ID NO:18:

(i) SEQUENCE CHARACTERISTICS:
        (A) LENGTH: 19 amino acids
        (B) TYPE: amino acid
        (C) STRANDEDNESS: unknown
        (D) TOPOLOGY: unknown (ii) MOLECULE TYPE: protein (ix) FEATURE:
        (A) NAME/KEY: Modified-site
        (B) LOCATION: 1
        (D) OTHER INFORMATION: /note= "The Xaa at position 1 can
            either be Tyrosine or Phenylalanine."

(ix) FEATURE:
        (A) NAME/KEY: Modified-site
        (B) LOCATION: 3
        (D) OTHER INFORMATION: /note= "The Xaa at position 3 can
            either be Glycine or Asparagine."

(ix) FEATURE:
        (A) NAME/KEY: Modified-site
        (B) LOCATION: 4
        (D) OTHER INFORMATION: /note= "The Xaa at position 4 can be
            any one of the following: Serine, Threonine, or Valine."

(ix) FEATURE:
        (A) NAME/KEY: Modified-site
        (B) LOCATION: 9
        (D) OTHER INFORMATION: /note= "The Xaa at position 9 can
            either be Isoleucine or Valine."

(ix) FEATURE:
        (A) NAME/KEY: Modified-site
        (B) LOCATION: 10
        (D) OTHER INFORMATION: /note= "The Xaa at position 10 can
            either be Isoleucine or Valine."

(ix) FEATURE:
        (A) NAME/KEY: Modified-site
        (B) LOCATION: 14
        (D) OTHER INFORMATION: /note= "The Xaa at position 14 can
            either be Methionine or Leucine."

(ix) FEATURE:
        (A) NAME/KEY: Modified-site
        (B) LOCATION: 15
        (D) OTHER INFORMATION: /note= "The Xaa at position 15 can be
            any one of the following: Leucine, Isoleucine, Valine or
            Cysteine."

(ix) FEATURE:
        (A) NAME/KEY: Modified-site
        (B) LOCATION: 17
        (D) OTHER INFORMATION: /note= "The Xaa at position 17 can
            either be Glycine or Alanine."

(ix) FEATURE:
        (A) NAME/KEY: Modified-site
        (B) LOCATION: 19
        (D) OTHER INFORMATION: /note= "The Xaa at position 19 can
            eitehr be Aspartic acid or Glycine."

(xi) SEQUENCE DESCRIPTION: SEQ ID NO:18:

```
Xaa Xaa Xaa Xaa Xaa Phe His Arg Xaa Xaa Xaa Xaa Phe Xaa Xaa Gln
1               5                   10                  15

Xaa Gly Xaa
```

(2) INFORMATION FOR SEQ ID NO:19:

(i) SEQUENCE CHARACTERISTICS:
  (A) LENGTH: 523 amino acids
  (B) TYPE: amino acid
  (C) STRANDEDNESS: unknown
  (D) TOPOLOGY: unknown (ii) MOLECULE TYPE: protein (xi) SEQUENCE DESCRIPTION: SEQ ID NO:19:

```
Met Gly Lys Lys Gln His Gln Lys Asp Lys Leu Tyr Leu Thr Thr Ser
1               5                   10                  15

Glu Trp Lys Ser Ile Gly Gly His Lys Asp Asp Thr Gly Thr Arg Leu
            20                  25                  30

Gln Arg Ala Gln Phe Lys Arg Leu Pro Ile Asn His Cys Ser Leu Ser
        35                  40                  45

Leu Leu Pro Phe Glu Asp Pro Val Cys Ala Arg Ser Gly Glu Ile Phe
50                  55                  60

Asp Leu Thr Ala Ile Val Pro Tyr Leu Lys Lys His Gly Lys Asn Pro
65                  70                  75                  80

Cys Thr Gly Lys Pro Leu Val Ala Lys Asp Leu Ile His Leu Lys Phe
            85                  90                  95

Asp Lys Gly Glu Asp Gly Lys Phe Arg Cys Pro Val Thr Phe Arg Thr
        100                 105                 110

Phe Thr Asp His Ser His Ile Leu Ala Ile Ala Thr Ser Gly Asn Val
    115                 120                 125

Tyr Ser His Glu Ala Val Gln Glu Leu Asn Leu Lys Arg Asn His Leu
130                 135                 140

Lys Asp Leu Leu Thr Asp Val Pro Phe Thr Arg Ala Asp Ile Ile Asp
145                 150                 155                 160

Leu Gln Asp Pro Asn His Leu Glu Lys Phe Asn Met Glu Gln Phe Leu
            165                 170                 175

His Val Lys Leu Asp Leu Lys Thr Ser Glu Glu Ile Lys Lys Glu Lys
        180                 185                 190

Asp Ala Met Lys Asp Pro Lys Phe Tyr Ile Arg Arg Met Asn Asn Ala
    195                 200                 205

Cys Lys Ser Val Leu Asp Gln Leu Asp Lys Glu Tyr Val Pro Lys Lys
210                 215                 220

Ser Thr Glu Thr Asp Glu Thr Ala Asp Glu Ile Asn Ala Ala His
225                 230                 235                 240

Tyr Ser Gln Gly Lys Val Ala Ala Gly Phe Thr Ser Thr Val Met Ala
            245                 250                 255

Pro Val Thr Ser Asn Lys Ala Ala Val Leu Asp Asn Asp Thr Val Arg
        260                 265                 270

Tyr Ser Arg Val Lys Lys Asn Ala Phe Val Arg Leu Val Thr Asn Phe
    275                 280                 285

Gly Pro Leu Asn Leu Glu Leu Phe Ala Pro Lys Val Pro Lys Ala Cys
290                 295                 300

Glu Asn Phe Ile Thr His Cys Ser Asn Gly Tyr Tyr Asn Asn Thr Lys
305                 310                 315                 320

Phe His Arg Leu Ile Lys Asn Phe Met Leu Gln Gly Gly Asp Pro Thr
            325                 330                 335

Gly Thr Gly His Gly Gly Glu Ser Ile Trp Asp Lys Pro Phe Ser Asp
        340                 345                 350

Glu Phe Ile Ser Gly Phe Ser His Asp Ala Arg Gly Val Leu Ser Met
    355                 360                 365
```

```
Ala Asn Lys Gly Ser Asn Thr Asn Gly Ser Gln Phe Phe Ile Thr Phe
370                 375                 380

Arg Pro Cys Lys Tyr Leu Asp Arg Lys His Thr Ile Phe Gly Arg Leu
385                 390                 395                 400

Val Gly Gly Gln Asp Thr Leu Thr Thr Ile Glu Lys Leu Glu Thr Glu
                405                 410                 415

Glu Gly Thr Asp Val Pro Met Val Ser Val Val Ile Met Arg Ala Glu
                420                 425                 430

Val Phe Val Asp Pro Phe Glu Glu Ala Glu Lys Glu Val Gln Ala Glu
                435                 440                 445

Arg Ala Glu Ile Leu Lys Lys Thr Ser Lys Asp Ala Ala Ser Leu Ala
450                 455                 460

Asn Lys Lys Ala Lys Glu Thr Ala Thr Lys Pro Glu Ala Val Gly Thr
465                 470                 475                 480

Gly Val Gly Lys Tyr Met Lys Ser Ala Ala Val Asn Lys Arg Gln
                485                 490                 495

Gly Lys Met Glu Asp Val Pro Leu Glu Ala Ala Lys Lys Thr Lys Phe
                500                 505                 510

Ala Arg Ala Gly Leu Gly Asp Phe Ser Lys Trp
515                 520
```

(2) INFORMATION FOR SEQ ID NO:20:

(i) SEQUENCE CHARACTERISTICS:
        (A) LENGTH: 1025 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:20:

```
CAGCAGGCTG CCTGATGACC ACTAGAGGTA TGTCTGCCCC TCGTCACCCT GCTGCACACC      60
AATCTGTGGC CCTTCATCAT GCTAAGAACA AGAACTGCGC CATGGCTGGC TCCTTCTCTT    120
CTCCAGCCCA TCCCTCTGCA GCCTGTCATC CCTGTCTGTG ACCATTGGTC GGGCCCCTGG    180
GCTCTAGAGT GACTTTTGAC GCCCTCCATC CCTCCCGCCA GGCACTGTCC TCCGCAAGGC    240
CTGGTGCAGC CCTGGCAGTA ACTGGCTTGT AAGAGGCTCA GACACCAAGC TGGGCCTGCA    300
GAGGAGGGGC ACAGTAGGAC ACAGTGACTG CCCAGGTGTC CACACACCTG TAGGCCTCTG    360
AGCCAGCGTC CAGGGTACAG ATGCGGGTGG TGGGGATGAA GGCCTGACCA GGGAGGGAGA    420
AGCAGGTTTG GAGAGGACCC TGTGCCCACC CTGACAGACA CCCTGGCTGG CCCTGACTGA    480
CTGTATTCTC TGGCCACATT CAAGTCCCCC ATTGGTGGGG GCAGAGAAGT AGGACCAGGC    540
CGTCCTTGGC TCCAGAGCTC GAAGACCCCA AGACAGCCCT CTGCTCTCAG CGGCGCCACA    600
GAGAGCCTGG GCTCAGCCTT CTGCATCAGG ACATGGCCTC GTCCACTGAG GCACGATTT     660
AAACATTTGA CATCAGAAGC TTTATTTGTA AACCTCACAC AGATAAGGAC CAAGGGCTGG    720
CGGTGTGGCC AGAGGACAGG GGAAGCTGAA GGCCCCGTGC TTGAGCTCGG CAGTCCTGCT    780
CCTTGCAGTG AAGCCACCAT GGGTGACCGT CCAGCCTCAC CCGGTGGCCT GCACAGTGAG    840
GGAAGGGCTT CAGGGCCATC TGCTCCCAGG GCAGGGGACA GGCCACCAAG GACCTTTGGC    900
AAATGAAGGT TTACATTTCT GTAGTTTGTT TGTTTTAGAG CTTAATTTGT AGTTTTTTAG    960
CTATTAAAAC CATTTGAATT TTTAACGACC TGATGAGGGC ATCAGGTAAA TTAAGGATT    1020
TTGAG                                                                1025
```

(2) INFORMATION FOR SEQ ID NO:21:

(i) SEQUENCE CHARACTERISTICS:
        (A) LENGTH: 1122 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:21:

```
CAGCAGCAAC TTGCAGGCTG TACCTCTGCC CTTCCTTTTC TCATCAATCA CTGATGCTGA      60

AGCTGCAGGC CTGAGCCCTT TGTCTCCCTG GATGCTGGGT GGCGCCTCAT CTGCATCTCT     120

GCCTCACCCC ATCCACTGCC ACAGGCTGCC TGATGACCAC TAGAGGTATG TCTGCCCCTC     180

GTCACCCTGC TGCACACCAA TCTGTGGCCC TTCATCATGC TAAGAACAAG AACTGCGCCA     240

TGGCTGGCTC CTTCTCTTCT CCAGCCCATC CCTCTGCAGC CTGTCATCCC TGTCTGTGAC     300

CATTGGTCGG GCCCCTGGGC TCTAGAGTGA CTTTTGACGC CCTCCATCCC TCCCGCCAGG     360

CACTGTCCTC CGCAAGGCCT GGTGCAGCCC TGGCAGTAAC TGGCTTGTAA GAGGCTCAGA     420

CACCAAGCTG GGCCTGCAGA GGAGGGGCAC AGTAGGACAC AGTGACTGCC CAGGTGTCCA     480

CACACCTGTA GGCCTCTGAG CCAGCGTCCA GGGTACAGGT GCGGGTGGTG GGGATGAAGG     540

CCTGACCAGG GAGTGAGAAG CAGGTTTGGA GAGGACCCTG TGCCCACCCT GACAGACACC     600

CTGGCTGGCC CTGACTGACT GTATTCTCTG GCCACATTCA AGTCCCCCAT TGGTGGGGGC     660

AGAGAAGTAG GACCAGGCCA TCCTTGGCTA CAGAGCTCGA AGACCCCAAG ACAGCCCTCT     720

GCTCTCAGCG GCGCCACAGA GAGCCTGGGC TCAGCCTTCT GCATCAGGAC ATGGCCTCGT     780

CCACTGAGGG CACGATTTAA ACATTTGACA TCAGAAGCTT TATTTGTAAA CCTCACACAG     840

ATAAGGACCA AGGGCTGGCG GTGTGGCCAG AGGACAGGGG AAGCTGAAGG CCCCGTGCTT     900

GAGCTCGGCA GTCCTGCTCC TTGCAGTGAA GCCACCATGG GTGACCGTCC AGCCTCACCC     960

GGTGGCCTGC ACAGTGAGGG AAGGGCTTCA GGGCCATCTG CTCCCAGGGC AGGGGACAGG    1020

CCACCAAGGA CCTTTGGCAA ATGAAGGTTT ACATTTCTGT AGTTTGTTTG TTTTAGAGCT    1080

TAATTTGTAG TTTTTTAGCT ATTAAAACCA TTTGAATTTT TA                       1122
```